United States Patent
Shi et al.

(10) Patent No.: US 12,403,163 B2
(45) Date of Patent: Sep. 2, 2025

(54) 3D PRINTED, FREEZE-DRIED HYDROGELS AND METHODS OF MAKING AND USING THE SAME

(71) Applicant: Iowa State University Research Foundation, Inc., Ames, IA (US)

(72) Inventors: Xiaolei Shi, Ames, IA (US); Stephanie Clark, Ames, IA (US); Hantang Qin, Ames, IA (US); Chih-Chun Kuo, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 17/813,190

(22) Filed: Jul. 18, 2022

(65) Prior Publication Data

US 2023/0084440 A1    Mar. 16, 2023

Related U.S. Application Data

(60) Provisional application No. 63/260,399, filed on Aug. 19, 2021.

(51) Int. Cl.
| | |
|---|---|
| *A61K 35/745* | (2015.01) |
| *A61K 9/06* | (2006.01) |
| *A61K 9/19* | (2006.01) |
| *A61K 47/36* | (2006.01) |
| *A61K 47/42* | (2017.01) |
| *B33Y 80/00* | (2015.01) |

(52) U.S. Cl.
CPC .............. *A61K 35/745* (2013.01); *A61K 9/06* (2013.01); *A61K 9/19* (2013.01); *A61K 47/36* (2013.01); *A61K 47/42* (2013.01); *B33Y 80/00* (2014.12)

(58) Field of Classification Search
CPC .. A61K 35/747; A61K 35/745; A61K 9/0056; A61K 9/06; A61K 47/36; A61K 47/42; A23L 29/20; A23L 33/135; A23P 30/00; B33Y 80/00
See application file for complete search history.

(56) References Cited

PUBLICATIONS

He et al (Crit. Rev. Food Sci. Nutr., 60(14):2379-2392 (2020), (Year: 2020).*
Liu et al., Food Bioprocess Technol., 12:267-279 (2019) (Year: 2019).*
Mallakpour et al., Adv. Coll. Interface Sci., 293(102436):1-28 (2021) (Year: 2021).*
Shavandi et al., Bioeng., 6(44):1-6 (2019) (Year: 2019).*
Yoha et al., LWT Food Sci. Technol., 146(111461):1-9 (2021) (Year: 2021).*
Martin-Dejardin et al., Euro. J. Pharma. Sci., 49:166-174 (2013) (Year: 2013).*
Li et al., J. Microencap., 26(4):315-324 (2009) (Year: 2009).*
Yao et al., Food Hydrocolloids, 72:228-236 (2017) (Year: 2017).*
Mathews., Int. J. Curr. Microbiol. App. Sci., 6(4):2080-2087 (2017) (Year: 2017).*
Alehosseini et al., Food Hydrocolloids, 87:487-496 (2019) (Year: 2019).*
Liu et al., J. Sci. Food Argic., 101:4398-4408 (2021) (Year: 2021).*
Szczesniak, Alina Surmacka, "Texture is a sensory property," Food Quality and Preferences, 2002, vol. 13, pp. 215-225.
Terpou et al., "Probiotics in Food Systems: Significance and Emerging Strategies Towards Improved Viability and Delivery of Enhanced Beneficial Value," Nutrients, 2019, vol. 11, No. 1591, pp. 1-32.
Tonon et al., "Physicochemical and morphological characterisation of açai (*Euterpe oleraceae* Mart.) powder produced with different carrier agents," International Journal of Food Science and Technology, Oct. 2009, vol. 44, Issue 10, pp. 1950-1958.
Tsen et al., "Survival of freeze-dried Lactobacillus acidophilus immobilized in k-carrageenan gel," The Journal of General and Applied Microbiology, 2002, vol. 48, No. 4, pp. 237-241.
Vancauwenberghe et al., "3D printing of plant tissue for innovative food manufacturing: Encapsulation of alive plant cells into pectin based bio-ink," Journal of Food Engineering, 2019, vol. 263, pp. 454-464.
Vancauwenberghe et al., "Pectin based food-ink formulations for 3-D printing of customizable porous food simulants," Innovative Food Science and Emerging Technologies, 2017, vol. 42, pp. 138-150.
Walls et al., "Yield stress and wall slip phenomena in colloidal silica gels," Journal of Rheology, Jul. 2003, vol. 47, No. 4, pp. 847-868.
Weinbreck et al., "Can encapsulation lengthen the shelf-life of probiotic bacteria in dry products?," International Journal of Food Microbiology, 2010, vol. 136, pp. 364-367.
Wilson et al., "Shear-Thinning and Thermo-Reversible Nanoengineered Inks for 3D Bioprinting," ACS Applied Materials & Interfaces, 2017, vol. 9, pp. 43449-43458.
Zhang et al., "3D printing of cereal-based food structures containing probiotics," Food Structure, 2018, vol. 18, pp. 14-22.
Zhang et al., "Fabrication and characterization of porous polycaprolactone scaffold via extrusion-based cryogenic 3D printing for tissue engineering," Materials and Design, 2019, vol. 180, No. 107946, pp. 1-10.
Akkasheh et al., "Clinical and metabolic response to probiotic administration in patients with major depressive disorer: A randomized, double-blind, placebo-controlled trial," Nutrition, 2016, vol. 32, pp. 315-320.

(Continued)

*Primary Examiner* — Michelle F. Paguio Frising
*Assistant Examiner* — Grant C Currens
(74) *Attorney, Agent, or Firm* — McKee, Voorhees & Sease, PLC

(57) ABSTRACT

The present disclosure relates to food grade hydrogels containing probiotics and methods of their preparation. More particularly, this disclosure describes 3D printable edible hydrogels, freeze-dried 3D printed edible hydrogels, systems for their printing, as well as, methods of preparing food grade 3D printed, freeze dried hydrogel compositions. Beneficially, the 3D printed, freeze-dried hydrogel compositions are storage stable.

12 Claims, 19 Drawing Sheets

(56) References Cited

PUBLICATIONS

Ambre et al., "Biomineralized hydroxyapatite nanoclay composite scaffolds with polycaprolactone for stem cell-based bone tissue engineering," Journal of Biomedical Materials Research Part A, 2015, vol. 103, No. 6, pp. 2077-2101.

Ambre et al., "In situ mineralized hydroxyapatite on amino acid modified nanoclays as novel bone biomaterials," Materials Science and Engineering C, 2011, vol. 31, pp. 1017-1029.

Ambre et al., "Nanoclay Based Composite Scaffolds for Bone Tissue Engineering Applications," Journal of Nanotechnology in Engineering and Medicine, Aug. 2010, vol. 1, pp. 1-9.

Ambre et al., "Nanoclays mediate stem cell differentiation and mineralized ECM formation on biopolymer scaffolds," Journal of Biomedical Materials Research Part A, 2013, vol. 101, No. 9, pp. 2644-2660.

Annan et al., "Encapsulation in alginate-coated gelatin microspheres improves survival of the probiotic Bifidobacterium adolescentis 15703T during exposure to simulated gastro-intestinal conditions," Food Research International, 2008, vol. 41, pp. 184-193.

Anukiruthika et al., "3D printing of egg yolk and white with rice flour blends," Journal of Food Engineering, 2020, vol. 265, No. 109691, pp. 1-11.

Burgain et al., "Encapsulation of probiotic living cells: From laboratory scale to industrial applications," Journal of Food Engineering, 2011, vol. 104, pp. 467-483.

Cassidy et al., "Survival and activity of lac-lux marked Pseudomonas aeruginosa UG2Lr cells encapsulated in K-carrageenan over four years at 4° C.," Journal of Microbiological Methods, 1997, vol. 30, pp. 167-170.

Castro et al., "Changes in the cell membrane of Lactobacillus bulgaricus during storage following freeze-drying," Biotechnology Letters, 1996, vol. 18, pp. 99-104.

Champagne et al., "Production of Concentrated Suspensions of Thermophilic Lactic Acid Bacteria in Calcium-alginate Beads," International Dairy Journal, 1993, vol. 3, pp. 257-275.

Cheng et al., "3D printing of extended-release tablets of theophylline using hydroxypropyl methylcellulose (HPMC) hydrogels," International Journal of Pharmaceutics, 2020, vol. 591, No. 119983, pp. 1-11.

Chung et al., "Bio-ink properties and printability for extrusion printing living cells," Biomaterials Science, 2013, vol. 1, pp. 763-773.

Collins, E. B., "Enumeration of Lactobacillus acidophilus with the Agar Plate Count," Journal of Food Protection, Jun. 1978, vol. 41, No. 6, pp. 439-442.

Cook et al., "Microencapsulation of probiotic bacteria into alginate hydrogels," in: Hydrogels in Cell-Based Therapies, Royal Society of Chemistry, 2014, pp. 95-11.

Dainty et al., "Stability of alginate-immobilized algal cells," Biotechnology and Bioengineering, Feb. 1986, vol. 28, Issue 2, pp. 210-216.

De Graef et al., "Chocolate yield stress as measured by oscillatory rheology," Food Research International, 2011, vol. 44, pp. 2660-2665.

Dianawati et al., "Survival of Microencapsulated Probiotic Bacteria after Processing and during Storage: A Review," Clinical Reviews in Food Science and Nutrition, 2016, vol. 56, pp. 1685-1716.

Freeman et al., "Biofabrication of Multiscale Bone Extracellular Matrix Scaffolds For Bone Tissue Engineering," European Cells and Materials, 2019, vol. 38, pp. 168-187.

Gao et al., "Optimization of gelatin-alginate composite bioink printability using rheological parameters: a systematic approach," Author manuscript, Biofabrication, 2018, vol. 10, No. 3, pp. 1-17.

Gooch, J. W., "Law of Mixtures," in: Encyclopedic Dictionary of Polymers, 2011, Springer, New York, NY.

Granato et al., "Functional Foods and Nondairy Probiotic Food Development: Trends, Concepts, and Products," Comprehensive Reviews in Food Science and Food Safety, May 2010, vol. 9, Issue 3, pp. 292-302.

Guidelines for the Evaluation of Probiotics in Food, Joint FAO (Food and Agriculture Organization of the United Nations) and WHO (World Health Organization) Working Group Report on Drafting Guidelines for the Evaluation of Probiotics in Food, London, Ontario, Canada, Apr. 30 and May 1, 2002, pp. 1-11.

Hamsupo et al., "Different Growth Media and Growth Phases Affecting on Spray Drying and Freeze Drying of Lactobacillus reuteri KUB-AC5," Agriculture and Natural Resources, 2005, vol. 39, No. 4, pp. 718-724.

He et al., "Research on the printability of hydrogels in 3D bioprinting," Scientific Reports, 2016, vol. 6, No. 29977, pp. 1-13.

Holkem et al., "Development and characterization of alginate microcapsules containing Bifidobacterium BB-12 produced by emulsification/internal gelatin followed by freeze drying," LWT—Food Science and Technology, 2016, vol. 71, pp. 302-308.

Hou et al., "Preparation of interconnected highly porous polymeric structures by a replication and freeze-drying process," Journal of Biomedical Materials Research, Part B, Applied Biomaterials, Nov. 2003, vol. 67B, Issue 2, pp. 732-740.

Hudson et al., "Characterization of the Probiotic Yeast *Saccharomyces boulardii* in the Healthy Mucosal Immune System," PLoS One, Apr. 11, 2016, vol. 11, No. 4, pp. 1-21.

Jasuja et al., "Perfusion bioreactor enabled fluid-derived shear stress conditions for novel bone metastatic prostate cancer testbed," Biofabrication, 2021, vol. 13, No. 035004, pp. 1-15.

Jiang et al., "Support Structures for Additive Manufacturing: A Review," Journal of Manufacturing and Materials Processing, 2018, vol. 2, No. 64, pp. 1-23.

Katti et al., "Use of unnatural amino acids for design of novel organomodified clays as components of nanocomposite biomaterials," Philosophical Transactions of The Royal Society A, 2010, vol. 368, pp. 1963-1980.

Kumar et al., "Probiotic metabolites as epigenetic targets in the prevention of colon cancer," Nutrition Reviews, 2013, vol. 71, No. 1, pp. 23-34.

Kuo et al., "An integrated manufacturing strategy to fabricate delivery system using gelatin/alginate hybrid hydrogels: 3D printing and freeze-drying," Food Hydrocolloids, 2021, vol. 111, No. 106262, pp. 1-10.

Kurtmann et al., "Water Activity-Temperature State Diagrams of Freeze-Dried Lactobacillus acidophilus (La-5): Influence of Physical State on Bacterial Survival during Storage," Biotechnology Progress, 2009, vol. 25, No. 1, pp. 265-270.

Lebeer et al., "Genes and Molecules of Lactobacilli Supporting Probiotic Action," Microbiology and Molecular Biology Reviews, Dec. 2008, vol. 72, Issue 4, pp. 728-764.

Li et al., "Rheological study on 3D printability of alginate hydrogel and effect of graphene oxide," International Journal of Bioprinting, 2016, vol. 2, No. 2, pp. 54-66.

Lin, David C., "Probiotics As Functional Foods," Nutrition in Clincal Practice, Dec. 2003, vol. 18, Issue 6, pp. 497-506.

Loebel et al., "Shear-thinning and Self-healing Hydrogels as Injectable Therapeutics and for 3D-Printing," Author Manuscript, Nature Protocols, Aug. 2017, vol. 12, No. 8, pp. 1521-1541.

Lopes et al., "Preparation and characterization of alginate and gelatin microcapsules containing Lactobacillus rhamnosus," Anais da academia brasileira de ciencias, 2017, vol. 89, No. 3, pp. 1601-1613.

Mugnier et al., "Survival of Bacteria and Fungi in Relation to Water Activity and the Solvent Properties of Water in Biopolymer Gels," Applied and Environmental Microbiology, Jul. 1985, vol. 50, No. 1, pp. 108-114.

Neffe-Skocinska et al., "Trends and Possibilities of the Use of Probiotics in Food Production," Alternative and Replacement Foods, 2018, Elsevier Inc., pp. 65-94.

Ooi et al., "Cholesterol-Lowering Effects of Probiotics and Prebiotics: A Review of in Vivo and in Vitro Findings," International Journal of Molecular Sciences, 2010, vol. 11, pp. 2499-2522.

Patarroyo et al., "Formulation and Characterization of Gelatin-Based Hydrogels for the Encapsulation of Kluyveromyces lactis—Applications in Packet-Bed Reactors and Probiotics Delivery in Humans," Polymers, 2020, vol. 12, No. 1287, pp. 1-23.

(56) References Cited

PUBLICATIONS

Pirbaglou et al., "Probiotic supplementation can positively affect anxiety and depressive symptoms: a systematic review of randomized controlled trials," Nutrition Research, 2016, vol. 36, pp. 889-898.

Potter et al., Food Science: Fifth Edition, Springer Science & Business Media, 2012, 608 pages.

Sarker et al., "Macromolecular interactions in alginate-gelatin hydrogels regulate the behavior of human fibroblasts," Journal of Bioactive and Compatible Polymers, 2017, vol. 32, No. 3, pp. 309-324.

Shori, Amal Bakr, "Microencapsulation Improved Probiotics Survival During Gastric Transit," Hayati Journal of Biosciences, 2017, vol. 24, pp. 1-5.

Silva et al., "Symbiotic microencapsulation to enhance Lactobacillus acidophilus survival," LWT—Food Science and Technology, 2018, vol. 89, pp. 503-509.

Sniffen et al., "Choosing an appropriate probiotic product for your patient: An evidence-based practical guide," PLoS One, 2018, vol. 13, No. 12, pp. 1-22.

Sun et al., "Extrusion-based food printing for digitalized food design and nutrition control," Journal of Food Engineering, 2018, vol. 220, pp. 1-11.

\* cited by examiner

3D PRINTED, FREEZE-DRIED HYDROGELS AND METHODS OF MAKING AND USING THE SAME

CROSS-REFERENCE

This application claims the benefit of Provisional Application U.S. Ser. No. 63/260,399 filed on Aug. 19, 2021, all of which is herein incorporated by reference in its entirety.

TECHNICAL FIELD

The present disclosure relates to food grade hydrogels containing probiotics and methods of preparation thereof.

BACKGROUND

Extruding, including types of 3D printing, is a popular method of manufacture in industry. 3D printing is a technology that fabricates designed, three dimensional objects in a manner of layer by layer under digital control. Over the past decades, 3D printing technology has obtained much attention in numerous fields due to its advantages of precisely controlled deposition, cost-effectiveness, simple processing, and fast prototyping. The application of 3D printing technology has been extended from plastic manufacturing to areas of civil construction, fashion and design, tissue engineering, pharmaceutical, and food production. Extrusion-based 3D printing is considered to be the ideal 3D printing technology for semi-solid or thermoplastic materials. The two most established extrusion-based 3D printing processes are fused deposition modeling (FDM) and semi-solid extrusion (SSE). FDM works mostly with thermoplastic material, which is extruded through the nozzle at a specific temperature to be meltdown into semi-molten filament, and then is deposited layer by layer on the build plate. As for semi-solid extrusion (SSE), a semi-solid material such as gel or paste is extruded at ambient temperature or slightly elevated temperature from a syringe-type nozzle under pressure to deposit a 3D structure. Unlike FDM, SSE extrudes out materials without the need for heating to melt the material, which is suitable for thermoset ingredients, such as hydrogels and many other biomaterials. Furthermore, SSE based 3D printing is suitable for soft materials with high viscosity; some examples including hydrogels, cell aggregates, and extracellular matrix.

3D printing technology has been applied in bioprinting to fabricate three-dimensional matrices to upload living cells, biomaterials, and active molecules, thus provide protection to the encapsulated active compounds. In the area of tissue engineering, hydrogels are primarily used as the bio-ink for bioprinting mainly due to its high-water content and biocompatibility. In addition, hydrogels can provide a viable microenvironment for the cell to attach, grow, and proliferate when used as the material for bioinks. Biopolymers such as collagen, gelatin, alginate, and chitosan are promising materials for extrusion-based 3D printing, as demonstrated by previous studies. Food-grade biopolymers such as gelatin and alginate could also be used as bioprinting materials in addition to thickening/gelling agents that are commonly used in the food industry. In addition, alginate hydrogels are applied to other areas such as encapsulation, cell transplantation, and tissue engineering. However, biopolymers, typically rely on ionic crosslinks which tend to break and re-form as the gel is strained, for example during 3D printing, resulting in permanent shape-change.

Rheological properties of the material on 3D printability should be taken into consideration when selecting the material for extrusion-based 3D printing. Viscosity, dynamic modulus and yield stress are important, indicating parameters of the printing quality during and after 3D printing process. Therefore, to satisfy the 3D printing purpose, the preferred ratio and concentration of the materials are the deciders for selected polymers. In addition, printing parameters, including the flow rate, printing speed, processing temperature, printing geometric, and infilled patterns, should be carefully controlled to attain the proper printing results.

Additional considerations need to be made when microorganism may be incorporated into the hydrogels. Probiotics are defined as "live microorganisms that, when administrated in adequate amounts, confer a health benefit on the host" (FAO/WHO, 2002). Health benefits of probiotics include enhancing the immune system, relieving diarrhea and symptoms of irritable bowel syndrome, preventing colon cancer, lowering cholesterol serum levels, and improving depression and anxiety disorder. In order to exert their health benefits to the host, probiotics should survive through the following factors: 1) manufacturing operations and storage conditions of the food products, 2) the digestive system, which involves: digestive enzymes, acidic environment, oxygen-rich environment, and the colonic microenvironment in the human gastrointestinal tract (GIT). Therefore, it is highly recommended that food products containing probiotic microorganisms should have at least $10^6$ CFU/g (CFU/mL) until the end of shelf life.

There is a need to develop new, customizable, and effective probiotic-containing products due to the following reasons. First, the market for probiotic foods is dominated by dairy-based products such as yogurt, cheese, and fermented milk. However, there are some challenges for such products. For example, dairy products are usually not shelf-stable and require low-temperature storage. Also, it is challenging to maintain their viability during long-term storage. In addition, due to the presence of lactose and milk protein, individuals with lactose intolerance or allergy may avoid dairy. Second, it has been suggested that the efficacy of probiotics is strain-specific and disease-specific, meaning that individuals with different health conditions will have disparate needs. Last, as consumers seek new products carrying the benefits of probiotics, the demand for innovative products is growing.

Encapsulation is a process that encapsulates the probiotic cells into a certain matrix or membrane to create a microenvironment in which the live cells can survive from the damaging factors in the surroundings. The goal for encapsulation is to protect the bacteria from adverse conditions during manufacture and storage, and in the digestive system. Carrier materials that are commonly used in the encapsulation of probiotics bacteria include polysaccharides (alginate, gums, chitosan, and K-carrageenan), protein (gelatin, whey protein, and milk protein), and fats. Gelatin is a protein derived from collagen that can form a gel by itself, and its amphoteric properties enable it to combine with other anionic polysaccharides to form a gel as well. Gelatin is also suitable for probiotic encapsulation when combined with other compounds or alone. Alginate is a polysaccharide extracted from algae and has been reported to be a good candidate for the encapsulation of probiotics due to its biocompatibility, biodegradability, and non-toxicity. A previous study reported that using alginate-gelatin microcapsules enabled *Lactobacillus rhamnosus* to reach the highest concentration of viable cells ($4.2 \times 10^9$ CFU/g) and maintain $10^5$ CFU/g concentration after four months of storage at 8°

C., which is below the recommended $10^6$ CFU/g for an effective probiotic. Also, alginate coated with gelatin microspheres provided significant protection for *Bifidobacterium adolescentis* 15703T from harsh gastrointestinal conditions. However, the permanent shape-change of biopolymers may be detrimental to microorganisms.

Therefore, there is a need to design new hydrogel-based matrices which are compatible with both manufacturing methods and with their components, such as microorganisms.

BRIEF SUMMARY OF PREFERRED EMBODIMENTS

This disclosure provides for 3D printable edible hydrogels, freeze-dried 3D printed edible hydrogels, and systems for printing and methods of printing the same. The advantages of the disclosed technologies are many.

Therefore, it is a primary object, feature, and/or advantage of this disclosure to improve on and/or overcome the deficiencies in the art. It is a further object of this disclosure to provide a printable hydrogel that is edible and storage stable upon freeze-drying. Another of the benefits of this disclosure is that the hydrogels can be printed from a variety of 3D printing mechanisms. Still another example of the benefit of this disclosure is that the hydrogel can comprise a probiotic. Other objects, features, and advantages of the invention can be identified by the description herein and the accompanying examples.

A preferred embodiment can be found in a method of preparing a shelf stable hydrogel, the method comprising obtaining a hydrogel precursor; mixing the hydrogel precursor with an active ingredient to form a mixture, wherein the active ingredient comprises a probiotic; crosslinking the hydrogel precursor into a hydrogel; 3D printing the hydrogel; and freeze-drying the hydrogel. Beneficially, the hydrogel can be food grade and the freeze-dried hydrogel is storage stable. In a preferred embodiment, the probiotic comprises a *Bifidobacterium* spp., *Lactobacillus* spp., a *Lactococcus* spp., and/or combinations thereof. In a preferred embodiment, the 3D printing is droplet-based, extrusion-based, stereolithography bioprinting, multi-printhead printing, or a combination thereof Still another preferred embodiment is a shelf-stable hydrogel composition, comprising a freeze-dried, 3D printed food grade hydrogel; the hydrogel comprising an active ingredient, wherein the active ingredient comprises a probiotic. Preferably, the freeze-dried hydrogel composition is shelf-stable for at least 3 months. In a preferred embodiment, the probiotic comprises a *Bifidobacterium* spp., *Lactobacillus* spp., a *Lactococcus* spp., and/or combinations thereof. In a preferred embodiment, the probiotic has a cell viability of at least about $10^6$ CFU/g after 3 months of storage.

These and/or other objects, features, and advantages of this disclosure will be apparent to those skilled in the art. The invention is not to be limited to or by these objects, features and advantages. No single embodiment need provide each and every object, feature, or advantage. While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

In FIG. 1 a syringe 10 can be viewed, which has a nozzle 20 and pressure 30 can be applied to extrude a printed object 50 comprised of the printable hydrogel composition 40 contained within the syringe 10.

DETAILED DESCRIPTION OF THE PREFERRED EMBODIMENTS

Figure 1:
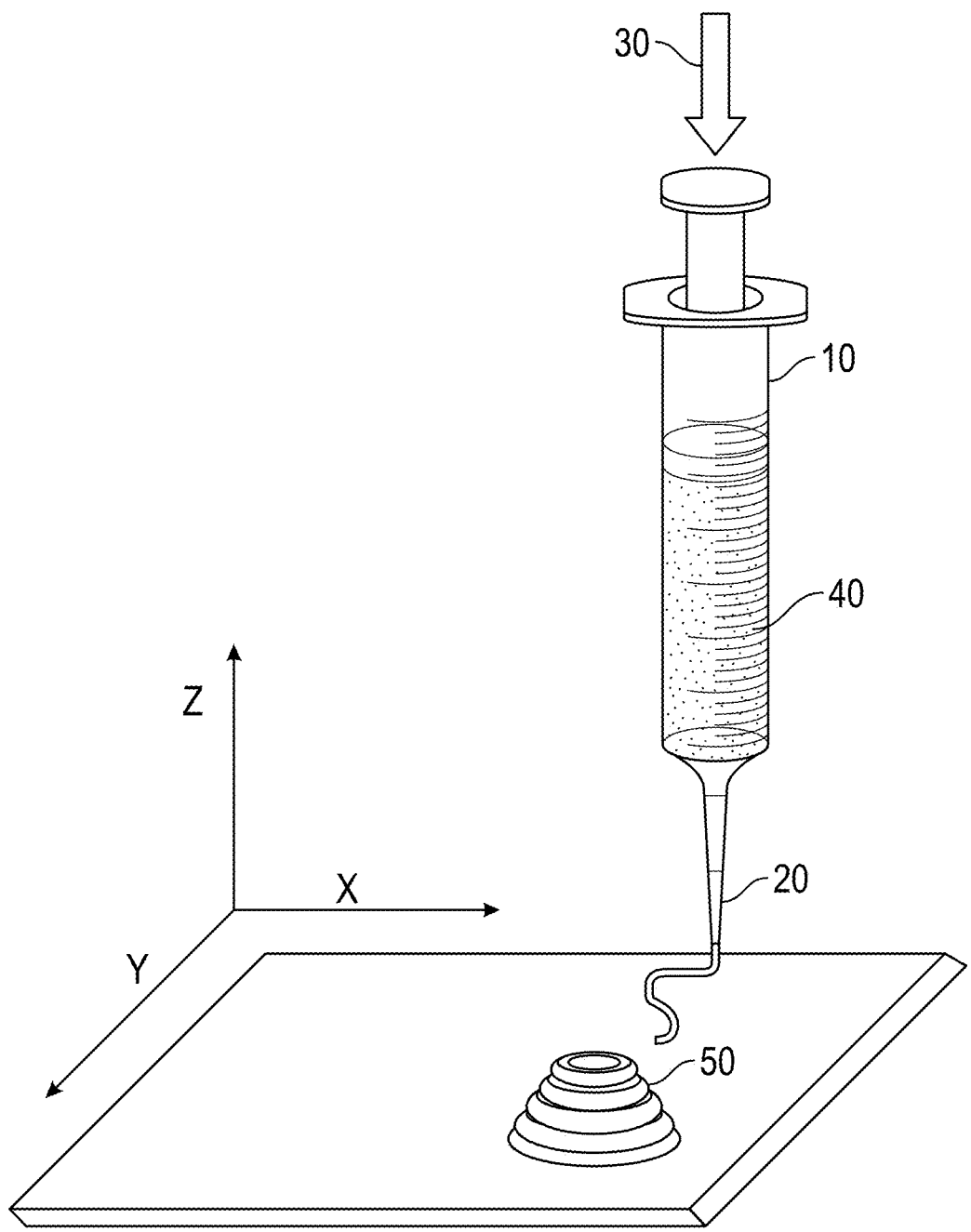
FIG. 1 shows a schematic of the extrusion-based 3D printer.

The present disclosure relates to probiotic and hydrogel compositions and methods of making thereof. The embodiments are not limited to particular methods and compositions depicted herein, which can vary and may be understood by skilled artisans. It is further to be understood that all terminology used herein is for the purpose of describing particular embodiments only and is not intended to be limiting in any manner or scope. Other objects, advantages and features of the present invention will become apparent from the following description taken in conjunction with the accompanying drawings.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

In order to provide a clear and consistent understanding of the specification and the claims, including the scope given to such terms, the following definitions are provided. Units, prefixes, and symbols may be denoted in their SI accepted form.

The term "about," as used herein, refers to variation in the numerical quantity that can occur, for example, through typical measuring techniques and equipment, with respect to any quantifiable variable, including, but not limited to, mass, volume, time, distance, rheology, viscosity, and population. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

As used herein, the term "administering" refers to the placement of a probiotic composition into a subject by a method or route which results in at least partial localization of the compound or composition to the gut or other hollow organ (e.g. oral cavity) such that a desired effect is produced. A composition described herein can be administered to the subject by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

As used herein, an "effective amount" or "therapeutically effective amount" refers to the amount of the probiotic composition and/or histamine degrading enzymes that is sufficient to prevent, treat, reduce and/or ameliorate the symptoms and/or underlying causes of a disorder or disease. In an exemplary aspect, an "effective amount" or "therapeutically effective amount" refers to the amount of probiotic that is sufficient to prevent, inhibit, and/or treat clostridial dermatitis, clostridial enteric disease, and/or gut inflammation in the gut of the subject, including farm production animals, companion animals, aquaculture and humans.

Also, as used herein, the term "gut" refers to the gastrointestinal tract as well as the liver, spleen, pancreas, omentum, and other organs served by the blood supply to and from the gut.

The term "microbiome", as used herein, refers to a population of microorganisms from a particular environment, including the environment of the body or a part of the body. The term is interchangeably used to address the population of microorganisms itself (sometimes referred to as the microbiota), as well as the collective genomes of the microorganisms that reside in the particular environment. The term "environment," as used herein, refers to all surrounding circumstances, conditions, or influences to which a population of microorganisms is exposed. The term is intended to include environments in a subject, such as a bird. Specifically, the term "intestinal microbiota", as used herein, refers to the population of microorganisms inhabiting the gastrointestinal tract. The term was previously referred to as the intestinal flora.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. The term "microbial" indicates pertaining to, or characteristic of a microorganism.

"Non-pathogenic bacteria" refers to bacteria that under normal conditions do not cause a disease or harmful responses in a healthy host. In some embodiments, non-pathogenic bacteria are commensal bacteria. Examples of non-pathogenic bacteria include, but are not limited to *Bacillus* spp., *Bacteroides* spp., *Bifidobacterium* spp., *Brevibacterium* spp., *Clostridium* spp., *Enterococcus* spp., *Escherichia coli, Lactobacillus* spp., *Lactococcus* spp., *Saccharomyces* spp., and *Staphylococcus* spp. Naturally pathogenic bacteria may be genetically engineered to provide reduced or eliminate pathogenicity according to standard methods in the art. Non-pathogenic bacteria may be genetically engineered to enhance or improve desired biological properties, e.g., survivability. Non-pathogenic bacteria and/or yeast may be genetically engineered to provide probiotic properties. Bacteria and/or yeast may be genetically engineered to be non-pathogenic. Without being limited to a particular mechanism of the invention, probiotics differ in their ability to produce neurochemicals in the gut of a subject. Non-pathogenic bacteria may be used for probiotic or synbiotic compositions used to treat subjects, while either pathogenic or non-pathogenic bacteria may be used for production of dopamine in a bioreactor or media. Pathogenicity, or virulence, of *E. faecium* may be defined as in the European Food Safety Authority, *Scientific Opinion on the safety and efficacy of Oralin® (Enterococcus faecium) as a feed additive for calves for rearing, piglets, chickens for fattening, turkeys for fattening and dogs*, EFSA Journal 2014; 12(6):3727, 19 pp. (doi:10.2903/j.efsa.2014.3727) in section 2.1.1.

The term "bioink", as used herein, refers to an aqueous hydrogel composition having an active ingredient and optionally an additive. Preferably the active ingredient is one or more of a probiotic, a prebiotic, an enzyme, or a vitamin. In a most preferred embodiment, the active ingredient comprises a probiotic. The optional additives may include, but are not limited to, a colorant, a flavor, and a scent.

"Probiotic" is used to refer to live, non-pathogenic microorganisms, e.g., bacteria which can confer health benefits to a host organism that contains an appropriate amount of the microorganism. In some embodiments, the host organism is a farm production animal, companion animal, aquaculture and/or human. Some species, strains, and/or subtypes of non-pathogenic bacteria are currently recognized as probiotics. Examples of probiotics include, but are not limited to, *Candida* spp., *Debaryomyces* spp., *Debaryomyces* spp., *Enterococcus* spp., *Kluyveromyces* spp., *Kluyveromyces* spp., *Saccharomyces* spp., *Yarrowia* spp., *Bifidobacteria* spp., *Escherichia coli, Vagococcus* spp., *Carnobacterium* spp., *Melissococcus* spp. and *Lactobacillus* spp., e.g., *Candida humilis, Debaryomyces* hansenii, *Debaryomyces occidentalis, Kluyveromyces lactis, Kluyveromyces lodderae, Kluyveromyces marxianus, Saccharomyces cerevisiae, Saccharomyces boulardii, Yarrowia lipolytica, Bifidobacterium bifidum, Enterococcus faecium, Enterococcus faecalis, Enterococcus hirae, Enterococcus casseliflavus, Enterococcus gallinarum, Escherichia coli* strain Nissle, *Lactobacillus acidophilus, Lactobacillus bulgaricus, Lactobacillus paracasei, Lactobacillus plantarum, Vagococcus fluvaialis* (Dinleyici et al., 2014; U.S. Pat. Nos. 5,589,168; 6,203,797; 6,835,376). A probiotic may also be a variant or a mutant strain of bacterium (Arthur et al., 2012; Cuevas-Ramos et al., 2010; Olier et al., 2012; Nougayrede et al., 2006).

By "treatment", "treat," "prevention," "prevent" or the like of an adverse condition, infection and/or disease is meant delaying or preventing the onset of such a condition, infection and/or disease, reversing, alleviating, ameliorating, inhibiting, slowing down or stopping the progression, aggravation or deterioration the progression or severity of a condition associated with such an adverse condition. In one embodiment, at least one symptom of an adverse condition is alleviated by at least 1%, at least 5%, at least 10%, at least 20%, at least 30%, at least 40%, or at least 50%.

The following is a list of reference numerals and their meanings:

| | |
|---|---|
| 10 | Syringe |
| 20 | Nozzle |
| 30 | Pressure |
| 40 | Printable hydrogel |
| 50 | Printed object |

It should be understood that these meanings are non-limiting and that the embodiment of FIG. 1 is intended to be a simplified example and non-limiting. Further, the ingredients that can be included in the printable hydrogel 40 are many and described in greater detail below, including, but not limited to, the hydrogel precursor, probiotic, additives, and active ingredients.

Hydrogel Precursors

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus, macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically, these reactions can be achieved through reacting molecules incorporating alcohol, amine, or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation, and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates. Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on a precursor. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. The hydrophilic precursor or precursor portion preferably has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic.

A precursor may also be a macromolecule (or macromer), which is a molecule having a molecular weight in the range of a few thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic polymers are free of amino acids or free of amino acid sequences that occur in nature. Some synthetic molecules are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Natural precursors may be used. Natural refers to biopolymers. Some natural precursors include polysaccharides, such as alginate and chitosan, polynucleotides, polypeptides, such as collagen and gelatin.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment and can change substantially according to the solvent or solutes around it, e.g., changes in temperature, pH, or ion content. Precursors may be dendrimers, e.g., as in Patent Application Pub. Nos. US20040086479, US20040131582, WO07005249, WO07001926, WO06031358, or the U.S. counterparts thereof; dendrimers may also be useful as multifunctional precursors, e.g., as in U.S. Pat. Pub. Nos. US20040131582, US20040086479 and PCT Applications No. WO06031388 and WO06031388; each of which US and PCT applications are hereby incorporated by reference herein in its entirety to the extent they do not contradict what is explicitly disclosed herein. Dendrimers are highly ordered possess high surface area to volume ratios and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus, a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group.

In a preferred embodiment the hydrogel precursor has a storage modulus (G') higher than loss modulus (G"), with a loss factor (tan δ=G"/G') in the range of 0.48 to 0.61 at the frequency sweep of 15 to 40 rad/s. In a most preferred embodiment, the methods and compositions comprising forming a hydrogel from two or more hydrogel precursors having a storage modulus (G') higher than loss modulus (G"), with a loss factor (tan δ=G"/G') in the range of 0.48 to 0.61 at the frequency sweep of 15 to 40 rad/s.

Hydrogel

They hydrogel may comprise of one or any combination of compatible precursors. Preferred hydrogels are food safe. More preferably, the precursors are biopolymers. Even more preferable, the precursors are alginate and/or gelatin.

For certain methods, the rheological properties of the hydrogel and its contents, such as but not limited to enzymes, probiotics, vitamins, and other nutraceuticals, should be considered. By way of non-limiting example, 3D printing and other extruding methods may require a certain range of viscosity to not plug the machinery during extrusion. In preferred embodiments, the range of viscosity is at least about 30 mPa/s to greater than $6 \times 10^7$ mPa/s. Other properties that may limit printability of the hydrogel may be the dynamic modulus and yield stress. In preferred embodiments, the storage modulus (G') is preferably greater than the loss modulus (G").

In some preferred embodiments, the hydrogel comprises of from about 0.1% to 20% w/w, from about 1% to about 15% w/w of a hydrogel precursor, or from about 1% to about 10% w/w of hydrogel precursor. If more than one precursor is used in a ratio from about 15:1 to about 1:15, from about 10:1 to about 1:10, or from about 5:1 to 1:5 depending on their effect on the rheological properties of the compositions.

In an even more preferred embodiment, the hydrogel comprises from about 1% to about 10% w/w, from about 1% to about 9% w/w, or from about 3% to about 7% w/w gelatin and alginate precursors combined in a ration from about 5:1 to about 1:5, from about 4:1 to about 1:4, or from about 2:1 to about 1:2.

Probiotics

Various strains are suitable for inclusion in the probiotic compositions and the listing of the genera name and representative strains are not meant to limit in any way that other strains belonging to that genus may be suitable probiotics. The various strains can also be given as a non-spore or as a spore. Exemplary microorganisms include: *Arthrobacter* spp., including for example *A. crystallopoietes*; *Bacillus* spp., including for example *B. subtilis, B. coagulans, B. lichenformis*, and *B. amyloliquefaciens*; *Bifidobactium* spp., including for example *B. adolescentis, B. animalis, B. breve, B. bifidum, B. lactis, B. longum*, and *B. angulatum*; *Brevibacterium* spp., including for example *B. linens*; *Micrococcus* spp.; *Rhizobium* spp.; *Enterococcus* spp., including for example *E. cecorum*; *Escherichia* spp., including for example *E. coli*; *Pseudomonas* spp., including for example *P. aeruginosa*; *Lactobacillus* spp., including for example *L. acidophilus, L. rhamnosus, L. sakei, L. plantarum*, and *L. crispatus*; *Lactococcus* spp., including for example *L. lactis, L. raffinolactis*; *Staphylococcus* spp., including for example *S. xylosus, S. caronusus*; *Agrobacterium* spp., including for example *A. tumefaciens*; *Vergibacillus* spp., including for example *V. halodenitrificans*; *Pseudomonas* spp., including for example *P. putida*; *Nocardioides* spp., including for example *N. simplex*; *Rummeliibacillus* spp., including for example *Rummeliibacillus stabekisii*; *Natrinema* spp., including for example *Natrinema gari*; *Debaryomyces* spp. (yeast), including for example *D. hansenii* (fungi); *Saccharomyces* spp. (yeast); and *Yarrowia* spp., including for example *Y. lipolytica*.

In a preferred embodiment and without limitation to use of other bacterial and yeast described herein, the probiotic compositions described herein include a *Bifidobacterium* spp., *Lactobacillus* spp. and/or a *Lactococcus* spp.

The probiotic may be added in sufficient quantity so that a minimum concentration of $10^6$ CFU/g is achieved for the shelf-life of the composition. In preferable embodiments, the shelf-life of the composition is about 3 months, about 4 months, or about 5 months, about 6 months, about 7 months, about 8 months, or about 9 months. Preferable starting concentrations of viable probiotic is about $10^8$ CFU/g, about $10^9$ CFU/g, about $10^{10}$ CFU/g, about $10^{11}$ CFU/g, about $10^{12}$ CFU/g or up to the saturation of the hydrogel.

Methods of Preparation

Another aspect of the disclosure is to provide a method of making a bioink composition, comprising of hydrogel precursors and optional ingredients, and 3D printing the bioink composition, the method comprising:

(a) obtaining one or more hydrogel precursors;
(b) optionally preparing two or more hydrogels from two or more hydrogel precursors by dissolving each precursor into deionized water, then combining the separately prepared hydrogels to form a bioink;
(c) optionally sterilizing the aqueous bioink;
(d) optionally centrifuging the aqueous bioink;
(e) optionally adding a one or more active ingredients and/or additives to the aqueous solution, to form an enriched bioink, wherein the active ingredients comprise a probiotic, a prebiotic, an enzyme, and/or a vitamin; wherein the additives comprise colorant, scent and/or flavoring;
(f) optionally centrifuging the enriched bioink;
(g) 3D printing the bioink;
(h) allowing the bioink to crosslink or set to re-form the hydrogel; and
(i) freeze drying the hydrogel.

Steps (a) to (f) represent the making of the bioink. The steps may be carried out at the same or different locations. Sterilization may be carried out on each hydrogel precursor, and each hydrogel precursor kept sterile, or after more than one hydrogel precursors are combined. One skilled in the art will appreciate that any sterilization should occur before any optional heat sensitive additive, such as a probiotic, is added to the hydrogel precursors.

Bioink Preparation

The bioink may be prepared by any method known in the art and depends on the hydrogel precursors. For example, if the resulting hydrogel comprises a single type of precursor, then the optional step of combing precursors may be skipped. In embodiments of multiple precursors, they may be combined by mixing, or more preferably, they may be separately formed into separate hydrogels, then the separate hydrogels can be combined. The single or combination of precursors may be diluted with an appropriate solvent, typically a polar solvent such as water or a polar organic solvent such as a short chain alcohol, to dilute the precursors to their desired concentration to form the bioink. In preferred embodiments the solvents is water, even more preferably deionized water. In a preferred embodiment, the method comprises mixing a hydrogel precursor with an active ingredient and optional additive to form a mixture. In an embodiment utilizing multiple hydrogel precursors, an active ingredient and optional additive can be mixed with each precursor or with a single precursor, then the respective hydrogels are formed, then the formed hydrogels are mixed.

In embodiments where more than one precursor is used for the preparation of the hydrogel and they are mixed together, air bubbles may form in the bioink due to the agitation. To remove the air, the hydrogel may be allowed to sit for a sufficient time for the air to rise to the top and leave the composition or more preferably, the composition may be spun at a sufficient speed to remove the air. In preferred embodiments, the mixed precursors may be spun in a centrifuge at 3000 rpm from about 1 minute to about 20 minutes, from about 2 minutes to about 20 minutes, or from about 2 minutes to about 15 minutes. Depending on the precursor, it may take longer to remove all air bubbled. The bioink may be centrifuged at about 1000 rpm, about 2000 rpm, about 3000 rpm, about 4000 rpm, about 5000 rpm or greater.

The bioink may be sterilized before or after air is removed through any means, such as baking, washing and/or dipping into a sterilizing agent, or autoclaving. Preferably, due to the liquid nature of the bioink, if sterilization is desired, it is done through autoclaving.

Optional ingredients may be added to the precursors before or after air is removed to form an enriched bioink. Optional ingredients include enzymes, probiotics, vitamins, and other nutraceuticals. In preferred embodiments, probiotics are added to the bioink, more preferably after any air has been removed from an initial centrifugation. To add a probiotic, the desired amount of probiotic may be pelleted to remove any supernatant due to growth media, freezing media, or from splitting media which may include trypsin or another proteolytic enzyme. The pellet may then be resuspended in the bioink by gentle mixing in order to not destroy the probiotic. In preferred embodiments of probiotic enriched hydrogels, the initial concentration of viable probiotic may be about $10^8$ CFU/g, about $10^9$ CFU/g, about $10^{10}$ CFU/g, about $10^{11}$ CFU/g, about $10^{12}$ CFU/g or up to the saturation of the hydrogel. The enriched bioink may then be centrifuged again to remove any air trapped in the bioink.

The bioink may then be either formed or be crosslinked into a hydrogel prior to 3D printing into a desired shape for packaging or further processing. To form the hydrogel, crosslinkers may be added to the solution if they are compatible with any additional ingredient in the bioink. Optionally, the bioink may be allowed to set over a period of time for crosslinking to occur. By way of nonlimiting example, the bioink may be allowed to set for 4 hours, 8 hours, 16 hours, 24 hours, 32 hours, or longer.

Shaping

The bioink or hydrogel may be formed into a desired shape using various methods. In some embodiments, the hydrogel may be shaped into a roll which may be further used to form sheets of hydrogel or as a sub-assembly for further processing, the bioink or hydrogel shaped pour-in-place, casting, extrusion, or 3D printing. Preferably, the hydrogel is extruded or 3D printed.

Any method of 3D printing may be used, for example droplet-based, extrusion-based, multi-printhead printing, or stereolithography bioprinting. Preferably, the hydrogels are formed using extrusion-based bioprinting.

Certain rheological properties of the bioink or hydrogel need to be met for formation into a desired shape. For example, if the hydrogel is too viscous, too much pressure may be needed to be applied to the extruder and the extruder may crack or break. However, if the bioink or hydrogel lacks stiffness it will not hold its shape after being formed. Formation of a desired shape of a hydrogel is highly related to the rheological properties, which can be quantitatively measured by a rheometer. For a discussion on rheological properties of cellulose-based hydrogels see U.S. application Ser. No. 17/301,695, which is hereby incorporated by reference herein in its entirety to the extent it does not contradict what is explicitly disclosed herein.

If the bioink was not crosslinked prior to shaping, it may be crosslinked during shaping or after using appropriate methods, such as UV crosslinking or the addition of cations.

Freeze Dry

After formation and/or crosslinking, the hydrogel is preferably freeze dried. Tablets were post-processed with freeze-drying. Without being bound by a specific theory, freeze-drying is believed to increase the shelf-stability and cell viability of the compositions by the removal of water from the hydrogel. Prior to freeze-drying, the hydrogel may be first frozen at 0° C.

After freeze drying, hydrogel enriched with probiotics preferably have at least about $10^8$ CFU/g, at least about $10^9$ CFU/g, at least about $10^{10}$ CFU/g, or at least $10^{11}$ CFU/g of viable probiotics.

The combination of freeze-drying and the printing pattern may be used to control the porosity of the hydrogel. Without being beyond by a particular theory, it is believed the colder the freeze dry temperature, the less porous the hydrogel will be due to the amount of dehydration.

EXAMPLES

Preferred embodiments of the present disclosure are further defined in the following non-limiting Examples. It should be understood that these Examples, while indicating certain preferred embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments described herein to adapt it to various usages and conditions. Thus, various modifications of the preferred embodiments of the disclosure, in addition to those shown and described herein, will be apparent to those skilled in the art from the foregoing description. Such modifications are also intended to fall within the scope of the appended claims.

Example 1

In this Example, the 3D printability of gelatin-alginate (G/A) hybrid hydrogels was investigated to obtain the preferred formula by adjusting the G/A ratio and the total solid concentration. After 3D printing, the semi-solid objects were post-processed by freeze-drying to solidify the matrices and make them shelf-stable. The microstructure was investigated by scanning electron microscopy (SEM) to evaluate the encapsulation capacity of the 3D printed matrix. Finally, the mechanical properties were assessed by texture profile analysis (TPA). Such matrices fabricated by 3D printing can be used to deliver the active compounds or cells for food or supplement production, such as enzymes, probiotics, vitamins, or other nutraceuticals, to promote human health.

Material and Methods

Material and Preparation

Gelatin Type-B, extracted from bovine skin with 225 Bloom, was provided by Sigma-Aldrich (St. Louis, MO). Sodium alginate (TICA-algin 400 Powder) was offered by TIC Gum (White Marsh, MD). Both polymers are food-grade ingredients. Hydrogel concentration (%) were narrowed down to 3-7% of the total solid content based on our preliminary experiment using a wider concentration range of 1-9%. The gelatin-alginate hydrogels with concentrations of 3%, 5%, and 7% (w/w) in total solid content were prepared using the following steps. First, gelatin particles and alginate powder were analytically weighted to the desired amount and mixed. Gelatin and alginate ratio were designed as 4:1, 2:1, 1:1, 1:2 and 1:4 (w/w). Second, deionized water was added to make 50 ml suspensions at three concentrations of 3%, 5%, and 7% (w/w in total solids). The gelatin-alginate mixtures were then homogenized by stirring manually while heating (60-70° C.) until the gelatin particles and alginate powders were completely dissolved and homogenized. Then, the gelatin-alginate mixtures were transferred into a 50 ml centrifuge tube and centrifuged at 3000 rpm for 10 min to remove the air bubbles, which were formed during the stirring process. To pre-test the 3D printability, approximately 10 ml of the samples were filled into a sterile syringe, which is the paste extruder for a 3D printer. All gelatin-alginate hydrogels were set for 24 hr for complete hydration and gelation before the rheology test and 3D printing process.

Rheological Properties

Rheological properties of the materials were carried out by Discovery HR-2 Rheometer (TA Instruments, New Castle, DE), according to Polamaplly et al. (2019), with minor modifications. All experiments were conducted at ambient temperature by using a 1 mm-gap size between geometry and Peltier plate with a 40 mm diameter of 2° cone-plate geometry. Measurements were accomplished with three deformation modes to determine the printability of the material. First, a flow ramp test was conducted at a constant temperature (20° C.) to study the flow behavior and viscosity of the material. Apparent viscosity ($\eta$) was examined with a function of shear rate ranging from 0.1 to 30.0 l/s. The first few points under low shear rate were deleted from the plot as they were out the trend. The yield stress (Pa) was estimated by the linear viscoelastic region (LVR). To determine the LVR of the materials, the amplitude stress sweep test was conducted within the oscillation strain range of 1-1000% in log mode at a constant frequency of 1.0 Hz. The plotted data were the products of the elastic modulus as a function of oscillation strain in a log-log transformation. The maximum value of the elastic stress curve could be explained as the yield stress. The storage modulus G', loss modulus G", and loss factor tan $\delta$ ($=G"/G'$) were measured by the oscillation frequency sweep test, during which the angular frequency accelerated from 0.1 to 100 rad/s at constant temperature (20° C.). The corresponding frequency can be related to the printing speed by using the equation of $\omega=v/r$, where $\omega$ is the angular frequency, $v$ is the 3D printing speed (=8 mm/s for our setting), and $r$ is the radius of the nozzle (=0.318 mm for our setting). All rheology analysis was conducted in triplicates.

3D Printing and Freeze-Drying

In this study, the 3D printing process was performed at ambient temperature by a customized extrusion-based 3D printer configured on the platform of the Velleman K8200 3D printer. (Velleman Inc., Fort Worth, Texas). A simplified schematic of the self-built extrusion-based 3D printer is illustrated in FIG. 1. The material was set inside the sterile syringe over 24 h before printing to ensure that they were well-hydrated and allowed the time for gelation. The geometric shape designed in this study simulated the shape of a chocolate drop (height=9.7 mm, diameter=16 mm) with a concentric infilled pattern. It was sliced into layers, and the G-code was generated by open-source Slic3r software. 3D printing parameters were described as followed: 0.636 mm of nozzle diameter, printing speed was 8.0 mm/s with the feed rate of 100 mm3/s, total layer numbers were 11 layers for each drop. After the 3D printing process, the 3D printed objects were post-processed with the freeze-drying technique. The printed objects were placed into a freezer (−30° C.) before freeze-drying. Then, the samples were put into a pilot freeze-dryer (Virtis Genesis SQ freeze dryer) in a condensation chamber under a low vacuum (below $2.6\times10^4$ Pa) for approximately 24 h.

Moisture content was measured by drying in an oven at 100±2° C. until reaching constant weight. Water activity values were measured by AquaLab 4 TE water activity meter (Decagon Devices, Washington, USA) at ambient temperature (25±1° C.). 3D printing repeatability and fidelity of 3D printed bioscaffold was determined by measuring the diameter and the height of the printed bioscaffold. The repeatability and accuracy of a 3D printed bioscaffold were compared with the designed shape (Diameter=1.6 cm, Height=0.97 cm) by measuring the diameter and the height of the 3D bioscaffold as indicated in Table 1. The 3D printed samples with >10% deviation were kicked out.

Texture Profile Analysis

After freeze-drying, the samples were characterized for texture profile conducted by a texture analyzer TA. XT plusC (Texture Technologies Corp. and Stable Micro System, Ltd. Hamilton, MA) at ambient temperature. Texture profiles for 3D printed objects before and after freeze-drying were measured with two sequential compression tests with an acrylic cylindrical plate probe (35 mm diameter). In addition, commercial food products were also evaluated to compare with our hydrogel samples. 3D printed hydrogels were compared with the commercial gummy probiotic supplement purchased from OLLY (San Francisco, CA), and freeze-dried hydrogels were compared with freeze-dried baby snacks: Yogurt Melts®, purchased from Gerber (Fremont, MI). Samples were compressed to 80% of their original height at a compression rate of 1 mm/s. Test setting was as follows: pre-test speed of 1.5 mm/s, test speed of 1 mm/s, post-test-speed 1.5 mm/s; trigger force of 10 g. The delay time between the first compression and the second compression was 5 s. All the analyses were carried out in triplicates for each type of formulations. The instrument software calculated seven texture characteristics: hardness (maximum force of the first compression), adhesiveness (area under the zero-force line which represents the amount of work needed to overcome attractive forces of the food to the compression plate), cohesiveness (the ratio of work done on the sample during the second bite divided by the work done on the sample during the first bite), springiness (now expressed as the ratio of product's original height: distance of the detected height during 2nd compression divided by original compression distance), gumminess (the product of cohesiveness times hardness), chewiness (the product of gumminess times springiness), and resilience (how sample recover from deformation in terms of speed and force), calculated by Stable Micro Systems' standard TPA macros.

Scanning Electron Microscope

Samples were analyzed by scanning electron microscope (SEM), JCM-6000SEM (Jeol, Japan) to observe the morphology of freeze-dried objects. Before scanning, samples were sputter-coated with gold for 60 s coating at 5-10 mA current in a vacuum chamber by to avoid charging problems during the electron scanning process. Then, the sample was transferred to the SEM, and high-quality images were taken at a magnification of 50× to 170×. The porosity was used to describe the empty space over the total volume.

Data Analysis

Statistical analysis was conducted using JMP Pro 14 (Cary, NC). Interaction effects of concentration and material ratio were statistically evaluated by fitting least squares and then computing in Tukey-Kramer HSD test. For texture profile analysis, the interaction between before and after freeze-drying was computed in the student's t-test. All experiments were performed in triplicate, and the results for the yield stress and texture profile analysis were presented as mean±standard deviation while the rheological data and its standard error were plotted as error bars. Significant differences at $p<0.05$ were applied to evaluate the differences between means. The hydrogel dimensions were presented in mean±standard deviation for diameter and height ($n=8$), and the outliers were deleted by the Dixon's Q test with a 95% confidence level.

Results and Discussion
Rheological Properties

Figure 2A:
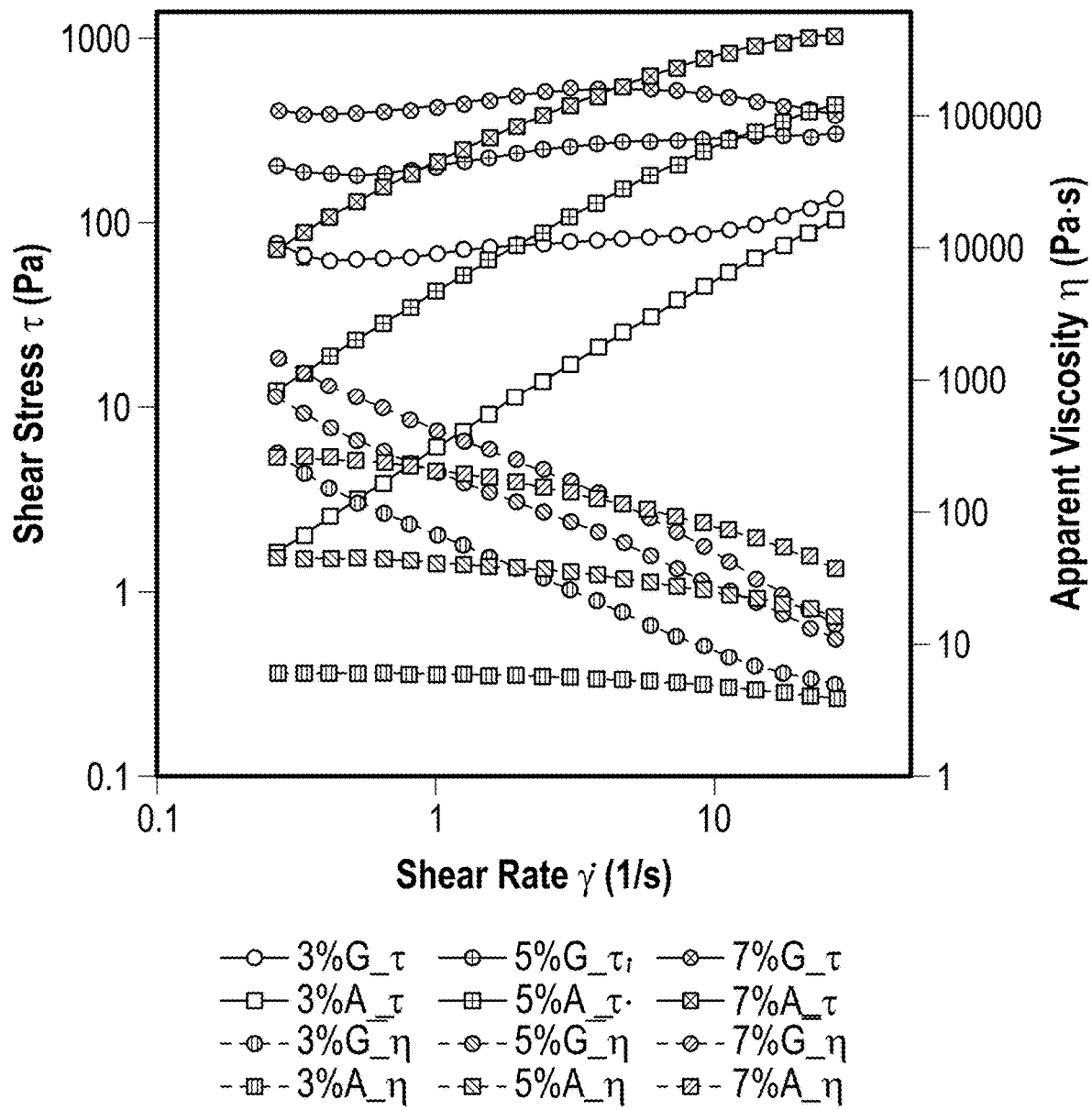
FIG. 2A shows the evolution of shear stress ($\tau$) and apparent viscosity ($\eta$) as function of shear rate ($\dot{\gamma}$) curve for pure gelatin and pure alginate with 3%, 5%, and 7%. The error bars represent mean±standard error of 3 replicates for all formulations.
Figure 2B:
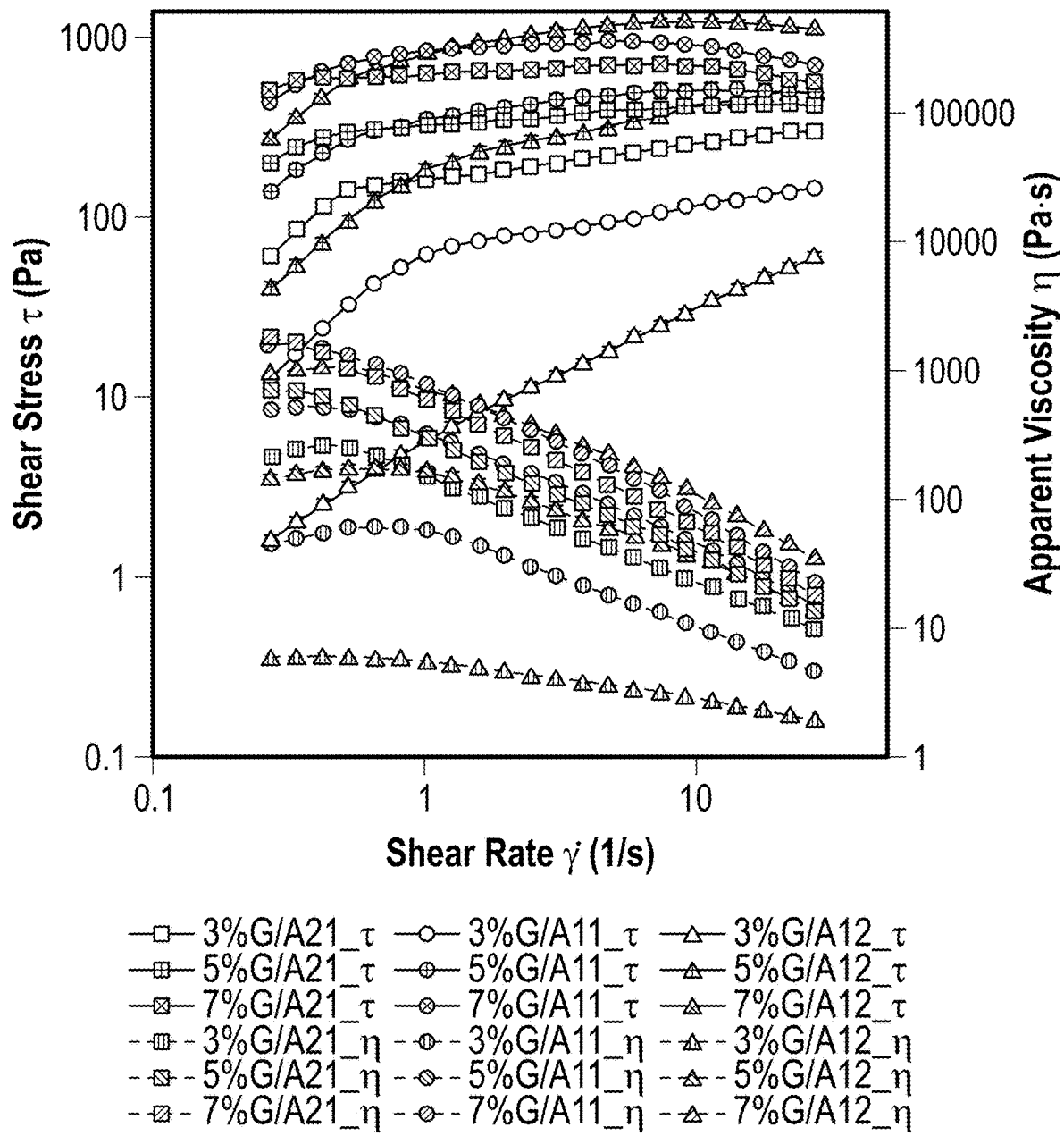
FIG. 2B shows the evolution of shear stress ($\tau$) and apparent viscosity ($\eta$) as function of shear rate ($\dot{\gamma}$) curve for gelatin-alginate hybrid matrix of 3% (G/A ratio 2:1, 1:1 and 1:2), 5% (G/A ratio 2:1, 1:1 and 1:2) and 7% (G/A ratio 2:1, 1:1 and 1:2). The error bars represent mean±standard error of 3 replicates for all formulations.

In this study, the flow behavior and apparent viscosity were analyzed by flow ramp test. FIGS. 2A and 2B show a log-log plot of stress and apparent viscosity versus shear rate for the hydrogels prepared by pure gelatin, pure alginate, and hybrid gels at different concentrations and by different ratios. FIG. 2A presented for pure gelatin and pure alginate with 3%, 5%, and 7% of total solid contents and were set as the control groups. On the other hand, FIG. 2B displayed the hybrid gelatin-alginate hydrogel matrix of 3%, 5%, and 7% of total solid content with G/A ratio 2:1, 1:1, and 1:2. The pure gelatin group displayed a shear-thinning behavior, as the apparent viscosity decrease with an increasing shear rate. Meanwhile, the apparent viscosity of the pure alginate was relatively constant with the increase of shear rate, showing a Herschel-Bulkley fluid behavior ($R2=0.99$). We further narrowed the data to see whether it fits into the Newtonian fluid model. In 3% of pure alginate, the R2 for the Newtonian fluid model was 0.98, and the R2 for 5% of pure alginate was 0.91. During our 3D printing experience, we found that the pure alginate with 3% and 5% were too liquid-like to sustain its shape after printing. In addition, hydrogel ink using pure gelatin alone was too brittle to be printed out. Therefore, based on the 3D printing results and rheological data, it was not feasible by using pure gelatin and pure alginate alone. In both pure gelatin and alginate, a higher concentration of the total solid resulted in higher apparent viscosity and stress under the same shear rate. In FIG. 2B, the formulation of 3%, 5%, and 7% gelatin-alginate matrix with G/A ratio 2:1, 1:1, and 1:2, all shown a shear-thinning behavior. For the material with the same total solid concentration of 3% and 5%, the stress and viscosity decreased as the G/A ratio increased. However, this trend was not significant in the case of 7%. The shear-thinning behavior of the material allowed them to be extruded out easily from a nozzle without clogging the nozzle head, as well as retaining the designed shape with high fidelity to form an integral structure after printed out. With this property, as long as a pressure higher than the yield stress is applied, these materials could be considered as the candidates for semi-solid extrusion 3D printing. Yield stress is another rheological parameter that may relate to the 3D printability of the material. A material should possess suitable yield stress and elastic modulus (G') to be regarded as printable and capable of holding the designed shape after deposition. Likewise, high yield stress at the point of the viscosity diminishing rapidly, corresponded to high printability of the material.

In this Example, the yield stress was estimated by the corresponding stress at the point of the end of LVR, which was marked as the first point when the storage modulus (G') declined by 10% of the G' within the LVR. Table 2 listed the estimated yield stress for 3%, 5% and 7% of gelatin-alginate mixture with pure gelatin, pure alginate, G/A ratio 2:1, 1:1, and 1:2. Under the same gelatin and alginate ratio, when increasing the total solid concentration, the yield stress increased significantly. There were significant differences between the control groups of pure gelatin and pure alginate. With the concentration of 3% and 7%, G/A ratio of 1:1 and 1:2 were not differed significantly, while differed from G/A 2:1 significantly. On the other hand, 5% of G/A 2:1 and 1:1 were not found significantly different in yield stress, but they are different from G/A 1:2.

Figure 3A:
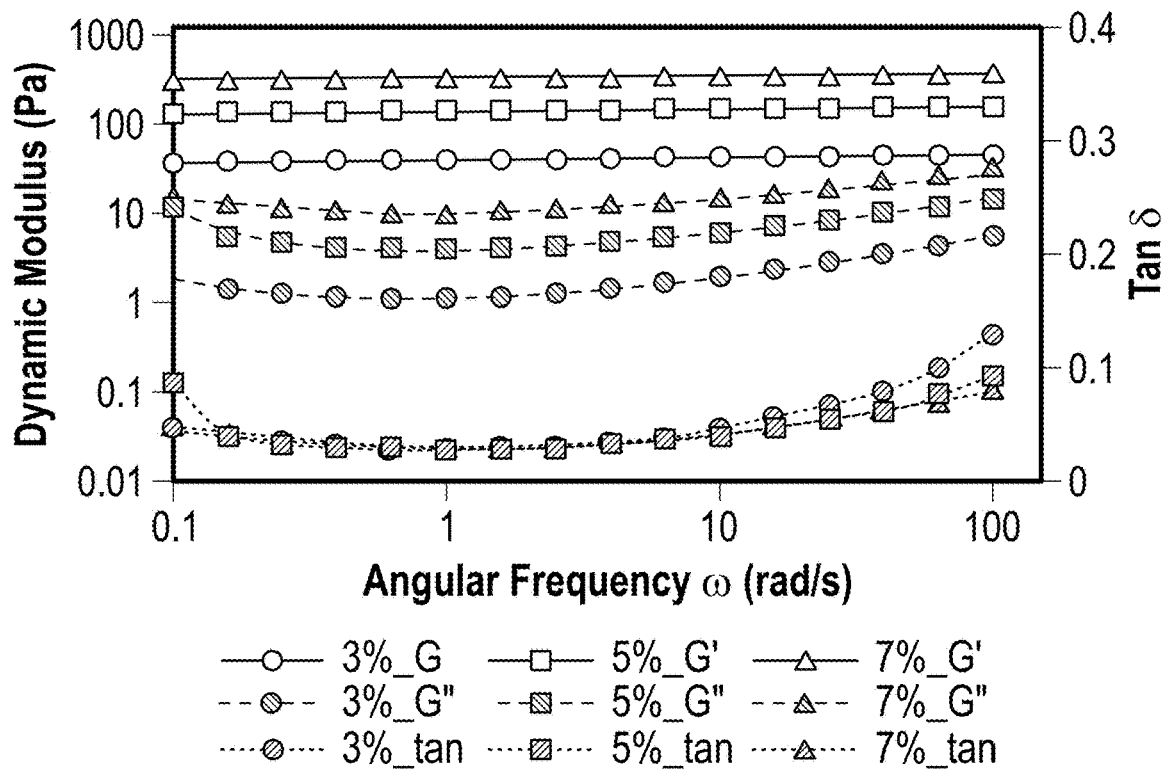
FIG. 3A shows the oscillation frequency sweep test: dynamic modulus and loss tangent versus angular frequency profiles of pure gelatin with 3%, 5%, and 7% concentration. The error bars represent mean±standard error of 3 replicates for all formulations.
Figure 3B:
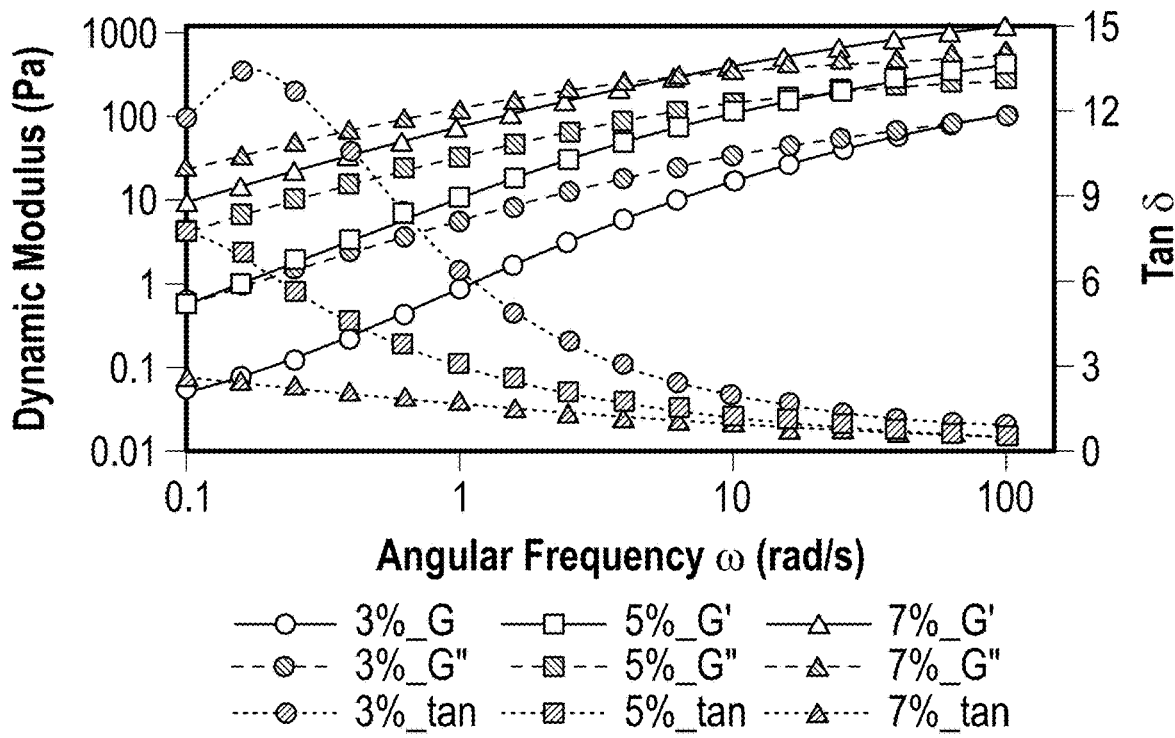
FIG. 3B shows the oscillation frequency sweep test: dynamic modulus and loss tangent versus angular frequency profiles of pure alginate with 3%, 5%, and 7% concentration. The error bars represent mean±standard error of 3 replicates for all formulations.
Figure 3C:
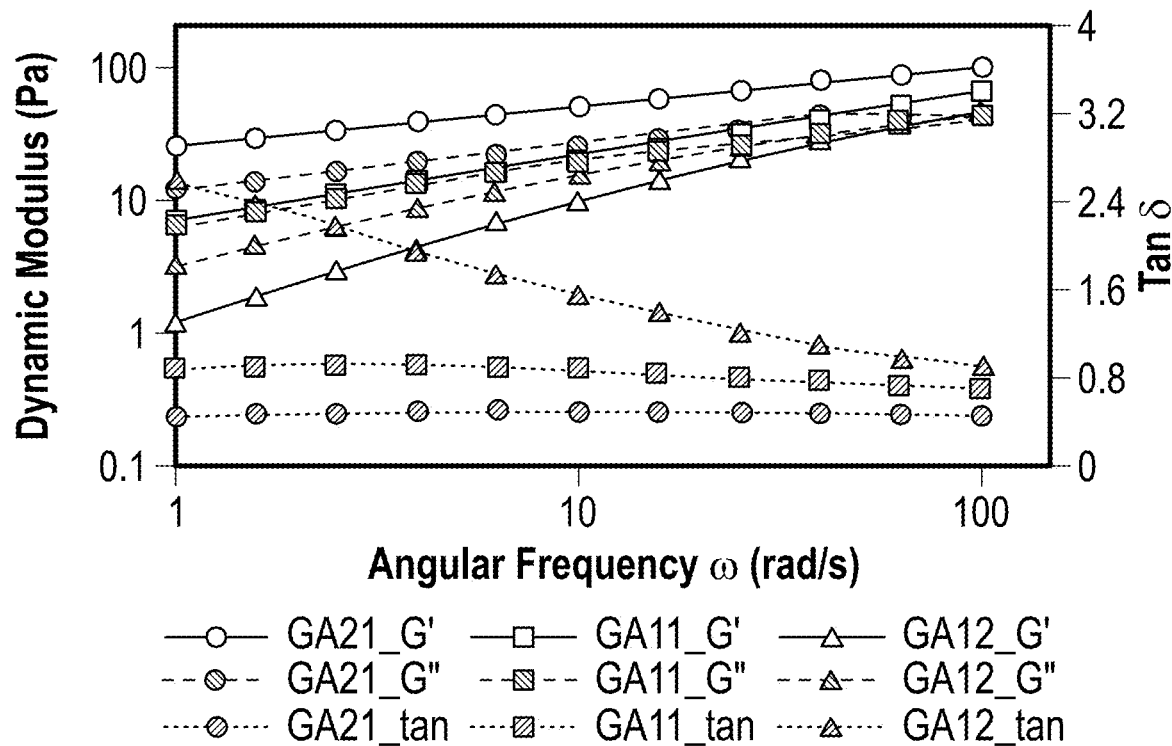
FIG. 3C shows the oscillation frequency sweep test: dynamic modulus and loss tangent versus angular frequency profiles of 3% of a gelatin-alginate mixture with G/A ratio 2:1, 1:1 and 1:2. The error bars represent mean±standard error of 3 replicates for all formulations.
Figure 3D:
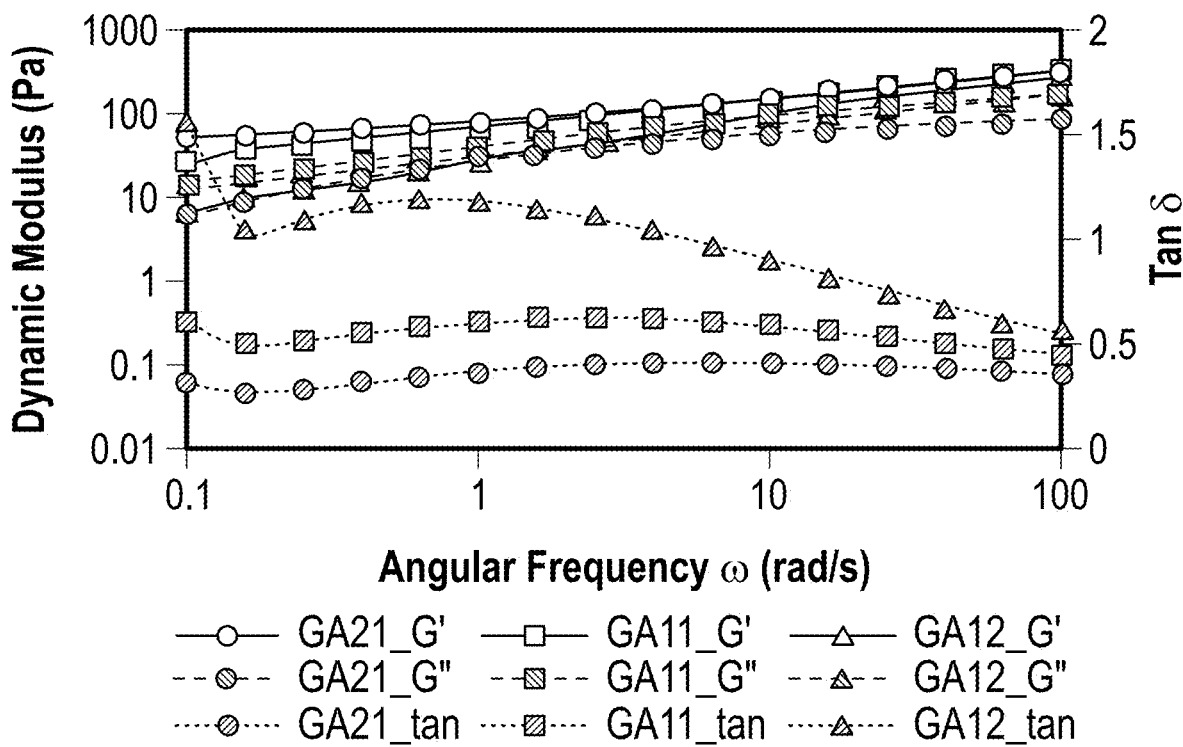
FIG. 3D shows the oscillation frequency sweep test: dynamic modulus and loss tangent versus angular frequency profiles of 5% of a gelatin-alginate mixture with G/A ratio 2:1, 1:1 and 1:2. The error bars represent mean±standard error of 3 replicates for all formulations.
Figure 3E:
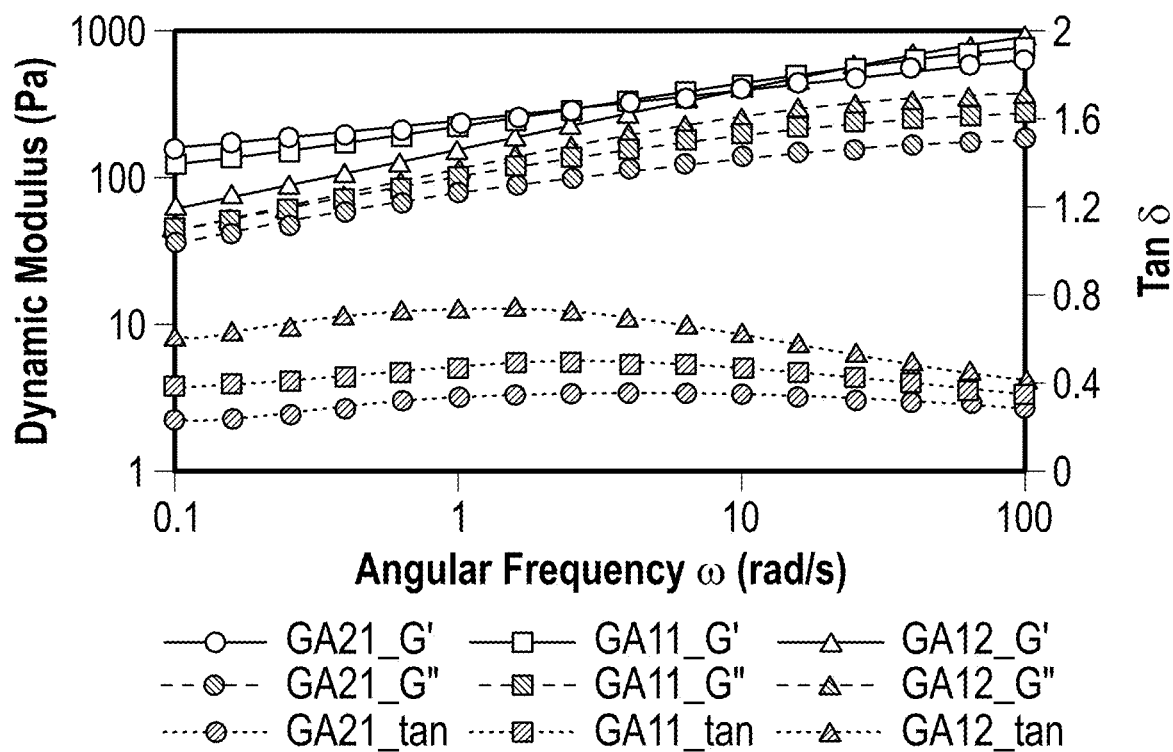
FIG. 3E shows the oscillation frequency sweep test: dynamic modulus and loss tangent versus angular frequency profiles of 7% of a gelatin-alginate mixture with G/A ratio 2:1, 1:1 and 1:2. The error bars represent mean±standard error of 3 replicates for all formulations.

Viscoelasticity is defined as a property of a material that exhibits both viscous (liquid-like) and elastic (solid-like) characteristics under the shear stress. Results of the oscillation frequency sweep test were presented in FIGS. 3A-3E. In the control groups (FIGS. 3A and 3B), the storage modulus (G') was always higher than the loss modulus (G"), and there was no crossover for pure gelatin (FIG. 3A). However, for pure alginate (FIG. 3B), the G" was higher than the G' at low sweep frequency, and then they crossed-over as the angular frequency increased. Among all tested samples (FIGS. 3C-3E), only 3% G/A 1:1 and 1:2 did not show a G' higher than the G" trend, while all of the other formulations did.

In addition, the parameter of tan δ is the ratio of G"/G' in viscoelastic materials. When tan δ is lower than 1, interpreting that the system is in an increase in elasticity and a decrease in plasticity. Materials with tan δ value within the range of 0.3-0.5 are mostly 3D printable. According to FIGS. 3C-3E, 3% G/A 2:1 and 1:1, 5% G/A 2:1 and 1:1, and 7% G/A 2:1, 1:1 and 1:2, all showed a tan δ value from 0.22 to 0.93, indicating that these materials were more solid-like. Additionally, the printable materials demonstrated a loss factor (tan δ=G"/G') in the range of 0.48-0.58 during the frequency sweep of 15-40 rad/s, which is the corresponding frequency that can be related to our 3D printing settings. In contrast, 3% G/A 1:2 and 5% G/A 1:2, with tan δ>1, representing a more liquid-like property. Without being bound by any particular theory, it is thought that the higher portion of alginate in the hydrogel formulation made the printing materials more viscous and flowable.

3D Printing and Freeze-Drying of Gelatin-Alginate Hybrid Hydrogel

Figure 8C:
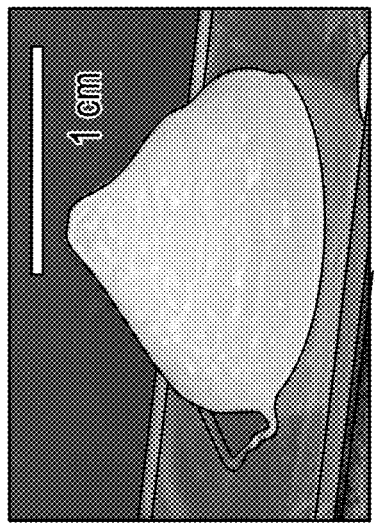
FIG. 8C shows an image of the 3D printed gelatin-alginate (G/A) hydrogel with a formulation of 3% G/A 2:1 encapsulated with *L. acidophilus* before freeze-drying.
Figure 8F:
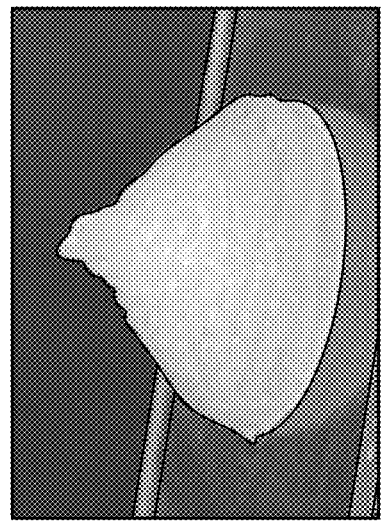
FIG. 8F shows an image of the 3D printed gelatin-alginate (G/A) hydrogel with a formulation of 5% G/A 1:1 encapsulated with *L. acidophilus* before freeze-drying.
Figure 8B:
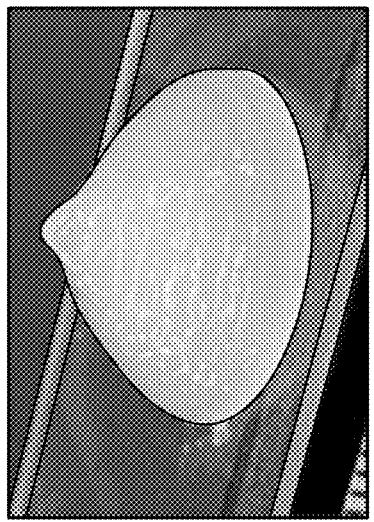
FIG. 8B shows an image of the 3D printed gelatin-alginate (G/A) hydrogel with a formulation of 3% G/A 1:1 encapsulated with *B. lactis* before freeze-drying.
Figure 8E:
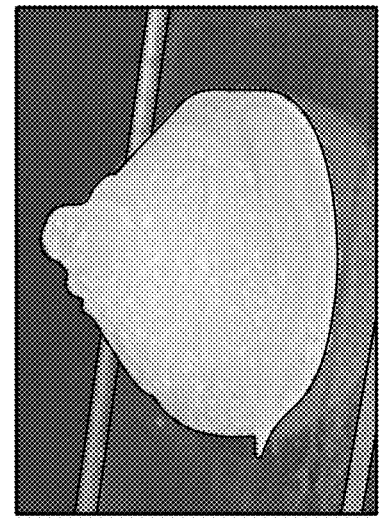
FIG. 8E shows an image of the 3D printed gelatin-alginate (G/A) hydrogel with a formulation of 5% G/A 1:1 encapsulated with *B. lactis* before freeze-drying.
Figure 8A:
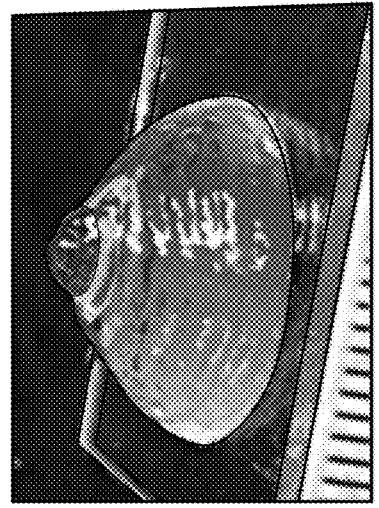
FIG. 8A shows an image of the 3D printed gelatin-alginate (G/A) hydrogel with a formulation of 3% G/A 2:1 without encapsulation or freeze-drying.
Figure 8D:
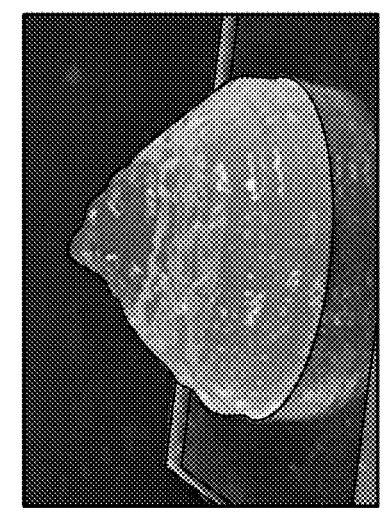
FIG. 8D shows an image of the 3D printed gelatin-alginate (G/A) hydrogel with a formulation of 5% G/A 1:1 without encapsulation or freeze-drying.
Figure 8I:
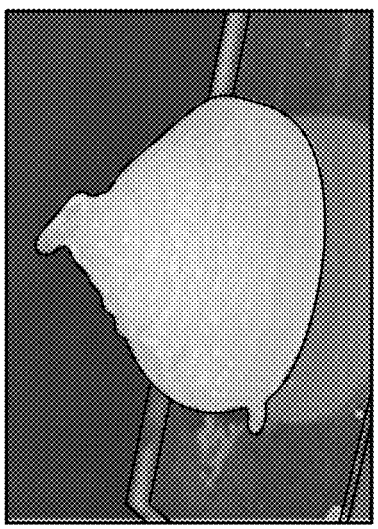
FIG. 8I shows an image of the 3D printed gelatin-alginate (G/A) hydrogel with a formulation of 7% G/A 1:2 encapsulated with *L. acidophilus* before freeze-drying.
Figure 8L:
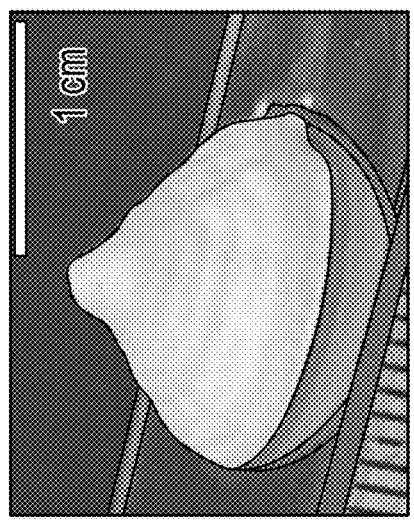
FIG. 8L shows an image of the 3D printed gelatin-alginate (G/A) hydrogel with a formulation of 3% G/A 2:1 encapsulated with *L. acidophilus* and after freeze-drying.
Figure 8H:
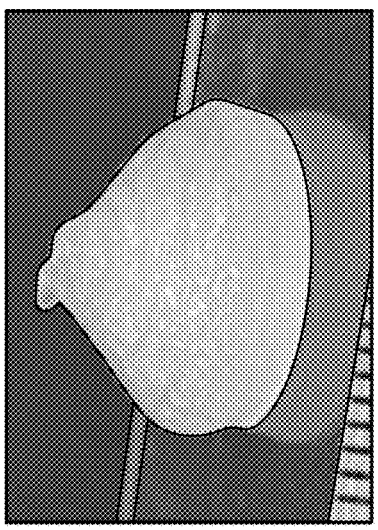
FIG. 8H shows an image of the 3D printed gelatin-alginate (G/A) hydrogel with a formulation of 7% G/A 1:2 encapsulated with *B. lactis* before freeze-drying.
Figure 8K:
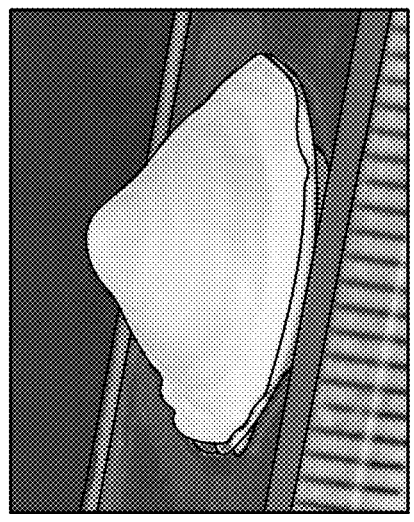
FIG. 8K shows an image of the 3D printed gelatin-alginate (G/A) hydrogel with a formulation of 3% G/A 2:1 encapsulated with *B. lactis* and after freeze-drying.
Figure 8G:
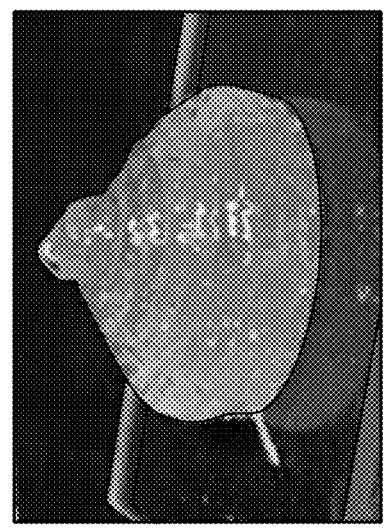
FIG. 8G shows an image of the 3D printed gelatin-alginate (G/A) hydrogel with a formulation of 7% G/A 1:2 without encapsulation or freeze-drying.

In our study, printability of a hydrogel material is defined as the following: (1) hydrogel ink should be continuously extruded out through a given diameter nozzle tip; (2) once being printed, the ink must possess sufficient mechanical strength to support its own weight and minimize deformation; (3) the layer-by-layer deposition should be uniformed and dimensionally stable during the whole printing process. In FIGS. 8A-8R, the 3D printed geometries were shown with the best printability of each total solid concentration: 3% of G/A 2:1, 5% G/A 1:1, and 7% G/A 1:2, respectively. To be considered 3D printable by an SSE extrusion-based 3D printer, the material must be easily extruded through the nozzle under specific pressure and should also possess enough mechanical strength to withstand the deformation. However, the material with high mechanical strength usually accompanies high viscosity and yield stress, which would block the nozzle during the extruding process, thus resulting in a printing failure. In our preliminary study, we evaluated the printability of 3%, 5%, and 7% of gelatin-alginate matrix with G/A ratio 4:1 and 1:4. However, we found that too high of the gelatin portion resulted in a fragile and brittle structure; meanwhile, the higher ratio of alginate reduced the viscosity significantly, making the printed objects unable to maintain its shape and thus flatten due to the low mechanical strength. Among the three geometries, 3% G/A 2:1, with the highest portion of gelatin and lowest total biopolymer concentrations, had the highest transparency. The explanation could be that the pure gelatin presented a vitreous and clear appearance with faintly yellow color. As the total solid content increased and the G/A ratio decreased, the transparency decreased, making 7% G/A 1:2 more opaque. This is due to the higher biopolymer content within the formulation. In addition, with a higher portion of alginate, the geometries had an appearance closer to pure alginate, which formed a colorless yet slightly cloudy, thick solution. 3% G/A 2:1 presented a jiggly, brittle, gel-like texture while 7% G/A 1:2 illustrated a smooth, flexible, and sticky texture. Moreover, 5% G/A 1:1 has the appearance closest to the initially designed geometry-a droplet. The repeatability and accuracy of our 3D printed hydrogel before and after freeze-drying are provided below in Table 1.

Table 1 Dimensions of the 3D printed hydrogel before and after freeze-drying with optimal formulations: 3% G/A 2:1, 5% G/A 1:1, and 7% G/A 1:2.

TABLE 1

Dimensions of the 3D printed hydrogel before and after freeze-drying with optimal formulations: 3% G/A 2:1, 5% G/A 1:1, and 7% G/A 1:2.

| Designed shape | Diameter (cm) 1.60 | | Height (cm) 0.97 | |
|---|---|---|---|---|
| | Before | After | Before | After |
| 3% G/A 2:1 | 1.66 ± 0.04 | 1.56 ± 0.12 | 0.96 ± 0.03 | 0.90 ± 0.06 |
| 5% G/A 1:1 | 1.61 ± 0.06 | 1.47 ± 0.07 | 0.99 ± 0.10 | 1.01 ± 0.06 |
| 7% G/A 1:2 | 1.65 ± 0.05 | 1.51 ± 0.09 | 0.92 ± 0.04 | 0.91 ± 0.07 |

Values are presented in mean ± standard deviation (n = 8).

Table 1 shows the dimension of the designed shape of the bioscaffold versus the 3D printed results of the hydrogel before and after freeze-drying with the optimal bio-ink formulations: 3% G/A 2:1, 5% G/A 1:1 and 7% G/A 1:2.

Figure 8J:
FIG. 8J shows an image of the 3D printed gelatin-alginate (G/A) hydrogel with a formulation of 3% G/A 2:1 without encapsulation and after freeze-drying.
Figure 8M:
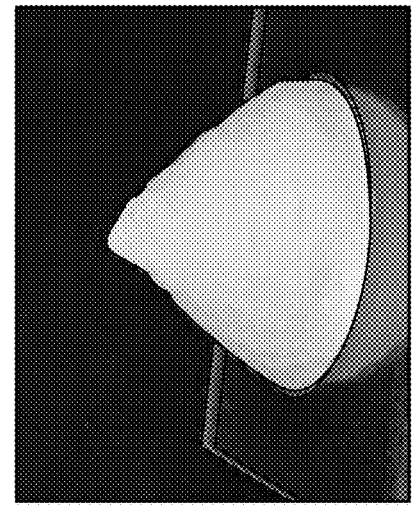
FIG. 8M shows an image of the 3D printed gelatin-alginate (G/A) hydrogel with a formulation of 5% G/A 1:1 without encapsulation and after freeze-drying.
Figure 8N:
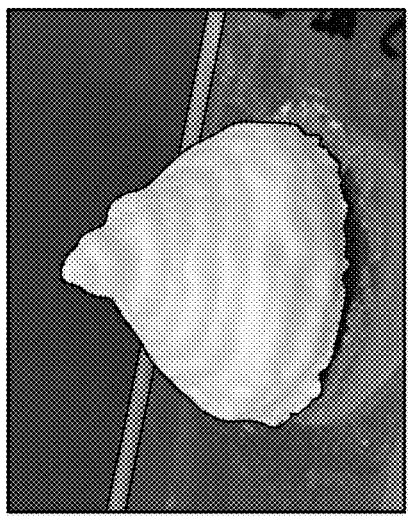
FIG. 8N shows an image of the 3D printed gelatin-alginate (G/A) hydrogel with a formulation of 5% G/A 1:1 with *B. lactis* after freeze-drying.
Figure 8O:
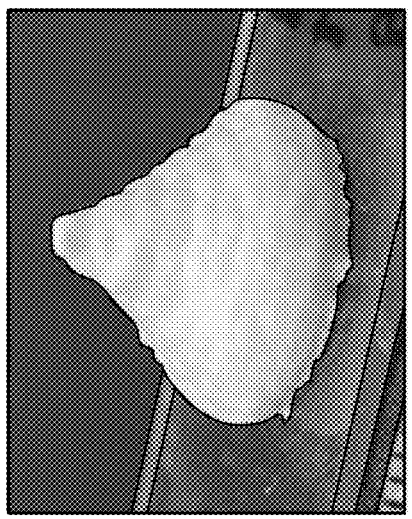
FIG. 8O shows an image of the 3D printed gelatin-alginate (G/A) hydrogel with a formulation of 5% G/A 1:1 encapsulated with *L. acidophilus* and after freeze-drying.
Figure 8P:
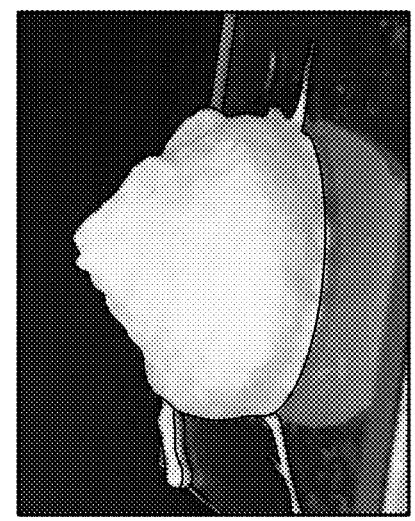
FIG. 8P shows an image of the 3D printed gelatin-alginate (G/A) hydrogel with a formulation of 7% G/A 1:2 without encapsulation and after freeze-drying.
Figure 8Q:
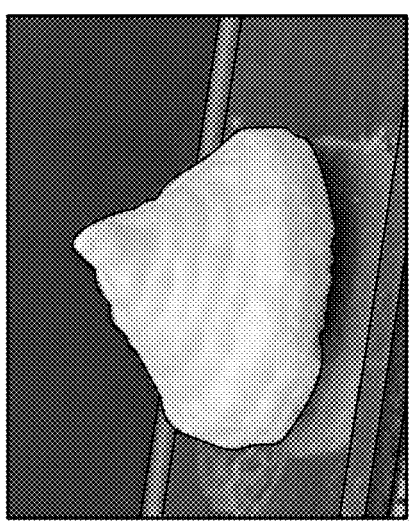
FIG. 8Q shows an image of the 3D printed gelatin-alginate (G/A) hydrogel with a formulation of 7% G/A 1:2 encapsulated with *B. lactis* and after freeze-drying.
Figure 8R:
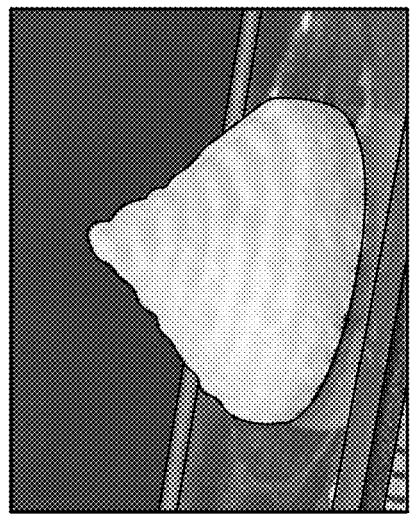
FIG. 8R shows an image of the 3D printed gelatin-alginate (G/A) hydrogel with a formulation of 7% G/A 1:2 encapsulated with *L. acidophilus* and after freeze-drying.

Images of the 3D printed geometries after freeze-drying with preferred formulations, 3% G/A 2:1, 5% G/A 1:1, and 7% G/A 1:2, were shown in FIGS. 8J, 8M, and 8P. After freeze-drying, the semi-solid hydrogels turned into an opaque, whitish appearance with low density. With little to no moisture content, the texture was similar to a Styrofoam, which was slightly harder than a sponge. One of the limitations of semi-solid extrusion-based 3D printing is that the printed product may require post-processing of drying or cooling, to make the printed objects shelf-stable and improve their mechanical properties. The freeze-drying allowed the printed objects to obtain an interconnected porous network with low density and crunchy texture. The integrated technology of 3D printing and freeze-drying may lead to the production of a novel snack food or supplement, which could be described as freeze-dried Jell-O-like material that is characterized by its crunchiness. This novel food has the potential to deliver customized types and amounts of fortified nutrients and supplements within its matrix.

Moisture content and water activity of the preferred gelatin-alginate hydrogel formulation: 3% G/A 2:1, 5% G/A 1:1, and 7% G/A 1:2, before and after freeze-drying were shown in Table 4. Before freeze-drying, the moisture content for 3% G/A 2:1, 5% G/A 1:1, and 7% G/A 1:2 were significantly different from each other. As the total solid concentration increased, the moisture content decreased. Since moisture content is a measurement of the total amount of water within the hydrogel, the lower total solid concentration will lead to a higher value of moisture content. However, after post-processing with freeze-drying, the moisture content dropped significantly to 0.03-0.04 (wt %), and there was no difference between the three groups after freeze-drying. On the other hand, water activity ($A_w$) is a measure of how efficiently the water can react chemically and physically and is calculated by the ratio of the vapor pressure in the hydrogel to the vapor pressure of the pure water. $A_w$ for the hydrogel before freeze-drying were 0.98 for 5% G/A 1:1 and 0.99 for 3% G/A 2:1 and 7% 1:2, and there was no difference between different groups. Meanwhile, after freeze-drying, the water activity significantly reduced to a value below 0.6 for all three groups. In general, a decrease in $A_w$ in foods represents a reduction in microbial growth, such as bacteria, yeast, molds, and some viruses and parasites. Particularly, when $A_w$ is lower than 0.6, no microorganism can grow. Therefore, the printed hydrogel will have a more stable and longer shelf-life after post-processing with freeze-drying.

Microstructure of 3D Printed Objects

Figure 4A:
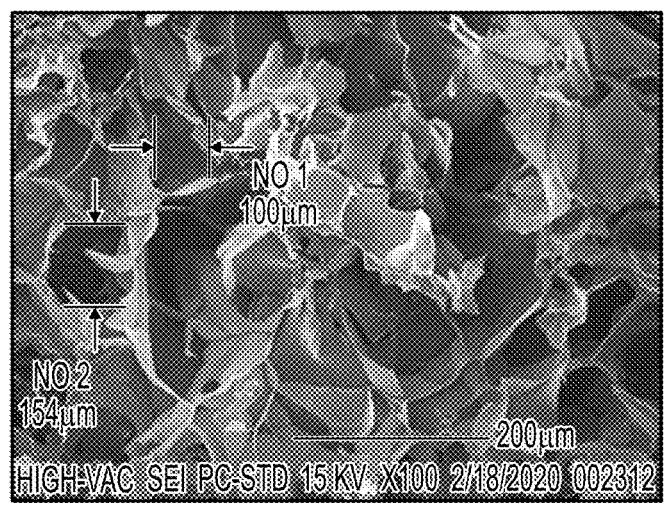
FIG. 4A shows an SEM magnification image of a longitudinal section of 3D printed geometries fabricated with 3% of pure gelatin.
Figure 4B:
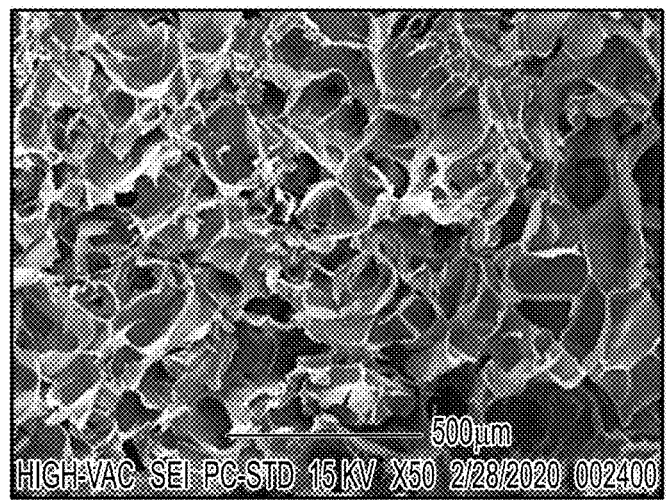
FIG. 4B shows an SEM magnification image of a longitudinal section of 3D printed geometries fabricated with 5% of pure gelatin.
Figure 4C:
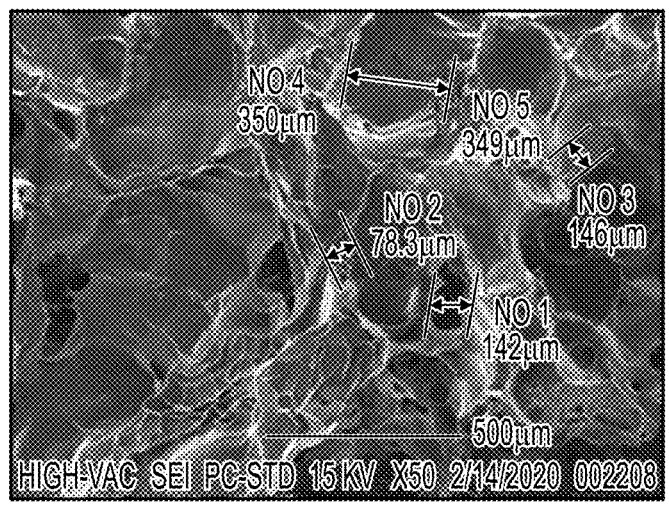
FIG. 4C shows an SEM magnification image of a longitudinal section of 3D printed geometries fabricated with 7% of pure gelatin.
Figure 4D:
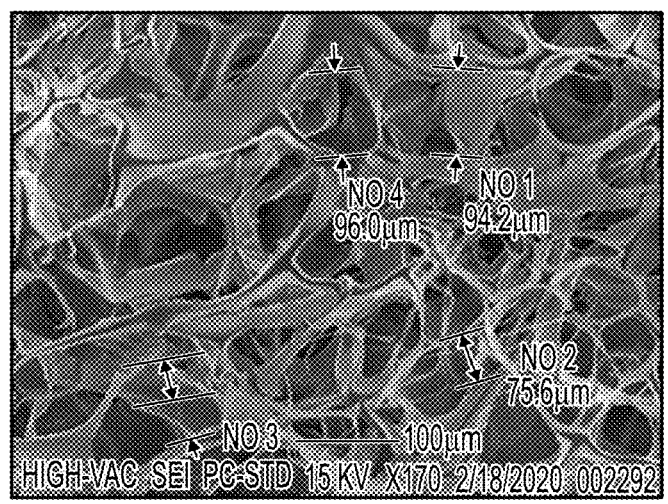
FIG. 4D shows an SEM magnification image of an overlook section of 3D printed geometries fabricated with 3% of pure alginate.
Figure 4E:
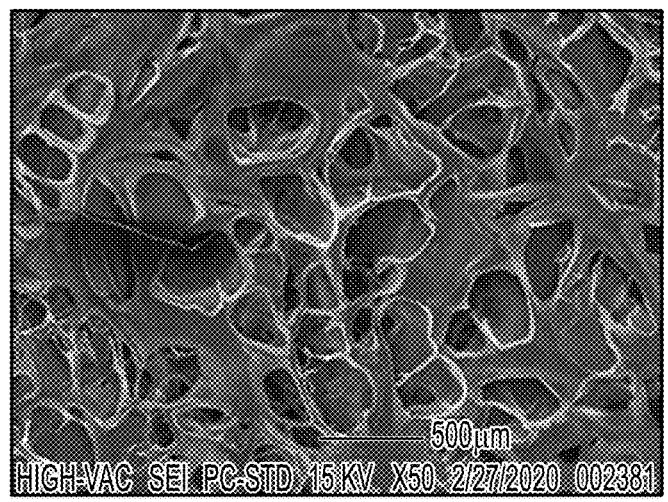
FIG. 4E shows an SEM magnification image of an overlook section of 3D printed geometries fabricated with 5% of pure alginate.
Figure 4F:
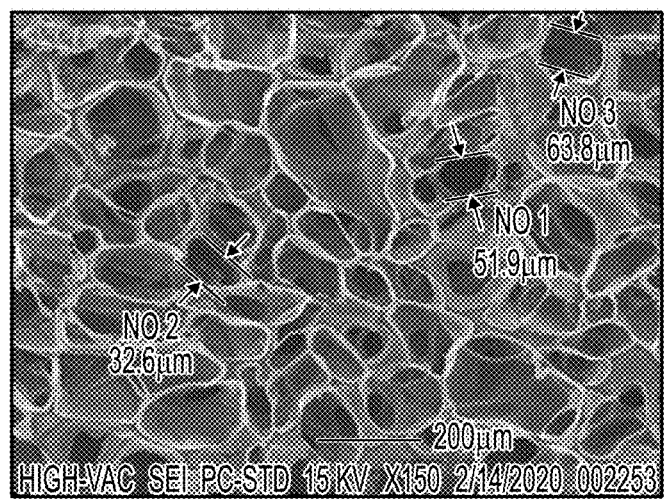
FIG. 4F shows an SEM magnification image of an overlook section of 3D printed geometries fabricated with 7% of pure alginate.
Figure 4G:
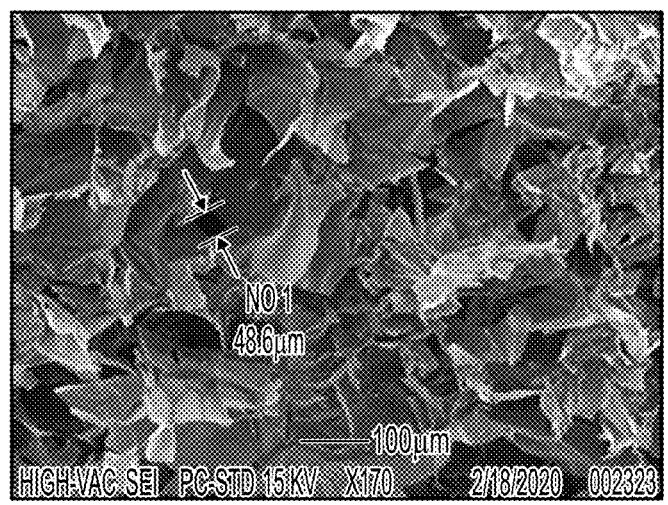
FIG. 4G shows an SEM magnification image of a longitudinal section of 3D printed geometries fabricated with 3% of gelatin-alginate mixture with G/A ratio 2:1.
Figure 4H:
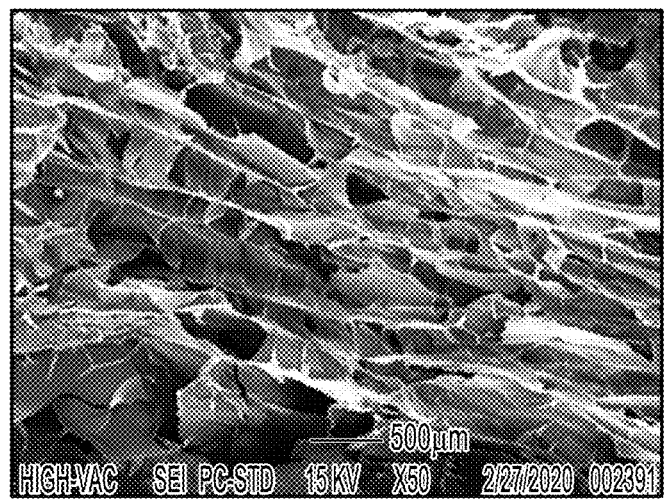
FIG. 4H shows an SEM magnification image of a longitudinal section of 3D printed geometries fabricated with 5% of gelatin-alginate mixture with G/A ratio 1:1.
Figure 4I:
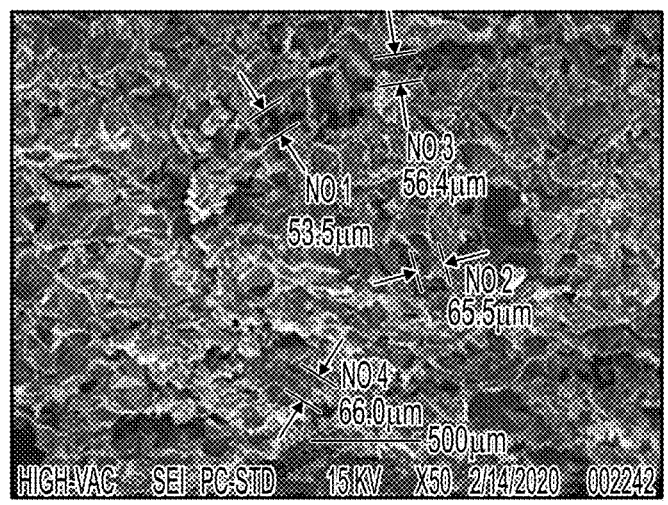
FIG. 4I shows an SEM magnification image of a longitudinal section of 3D printed geometries fabricated with 7% of gelatin-alginate mixture with G/A ratio 1:2.
Figure 5A:
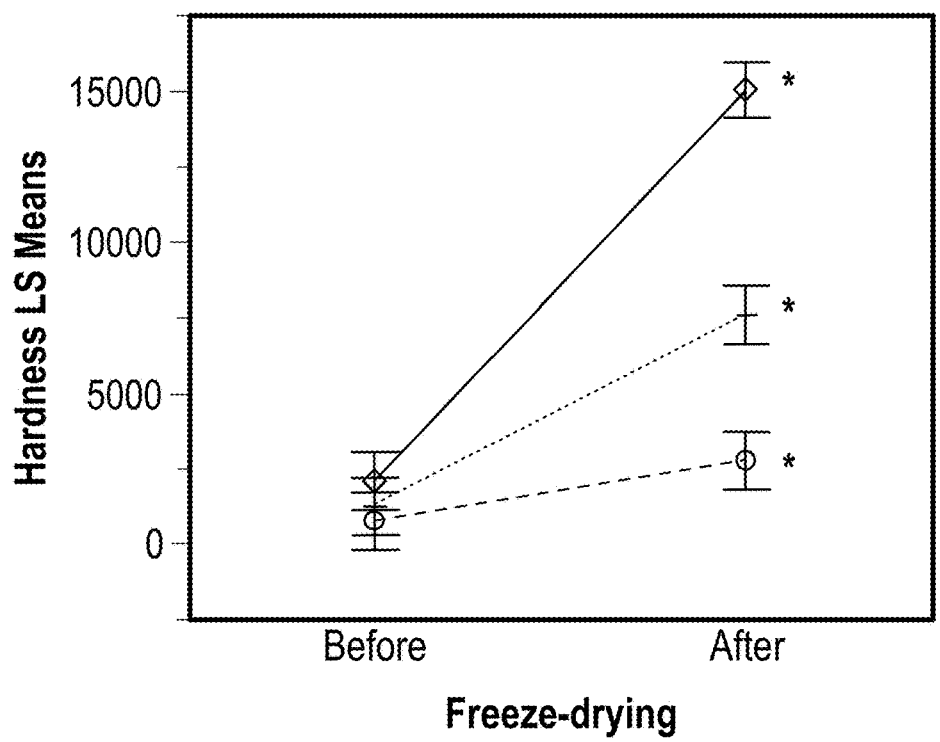
FIG. 5A shows a texture profile analysis, specifically looking at hardness, of the 3D printed hydrogels before and after freeze-drying for the three optimal formulations in a least squares means plot. *: significant difference ($p<0.05$) was found within the same group before and after freeze-drying.
Figure 5B:
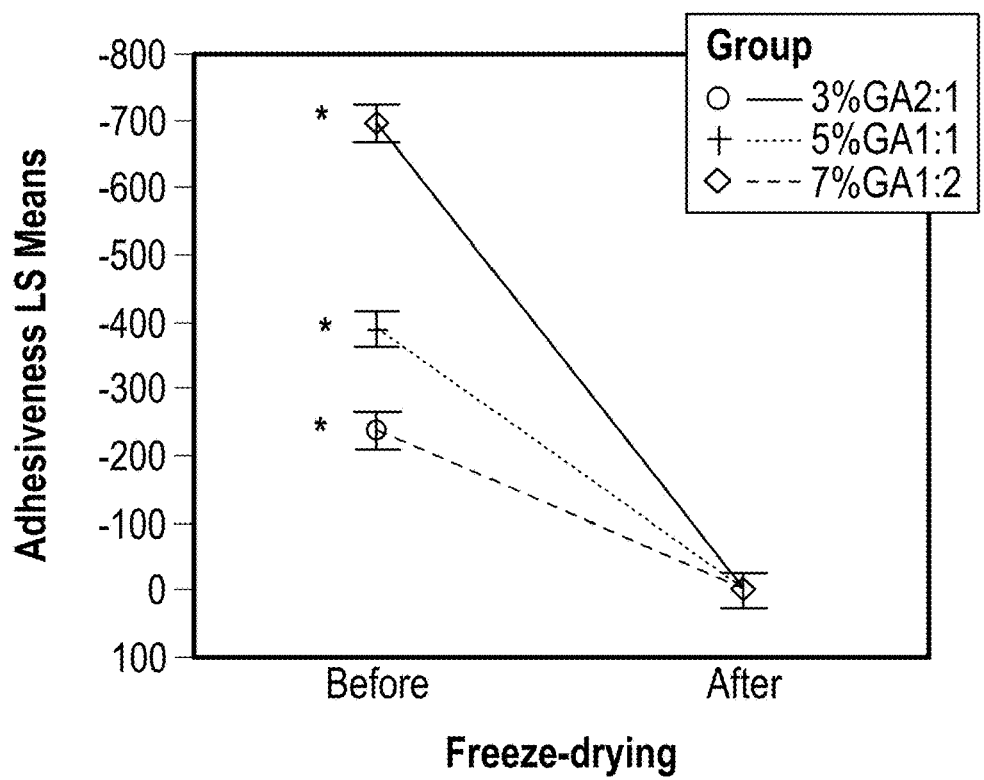
FIG. 5B shows a texture profile analysis, specifically looking at adhesiveness, of the 3D printed hydrogels before and after freeze-drying for the three optimal formulations in a least squares means plot. *: significant difference ($p<0.05$) was found within the same group before and after freeze-drying.
Figure 5C:
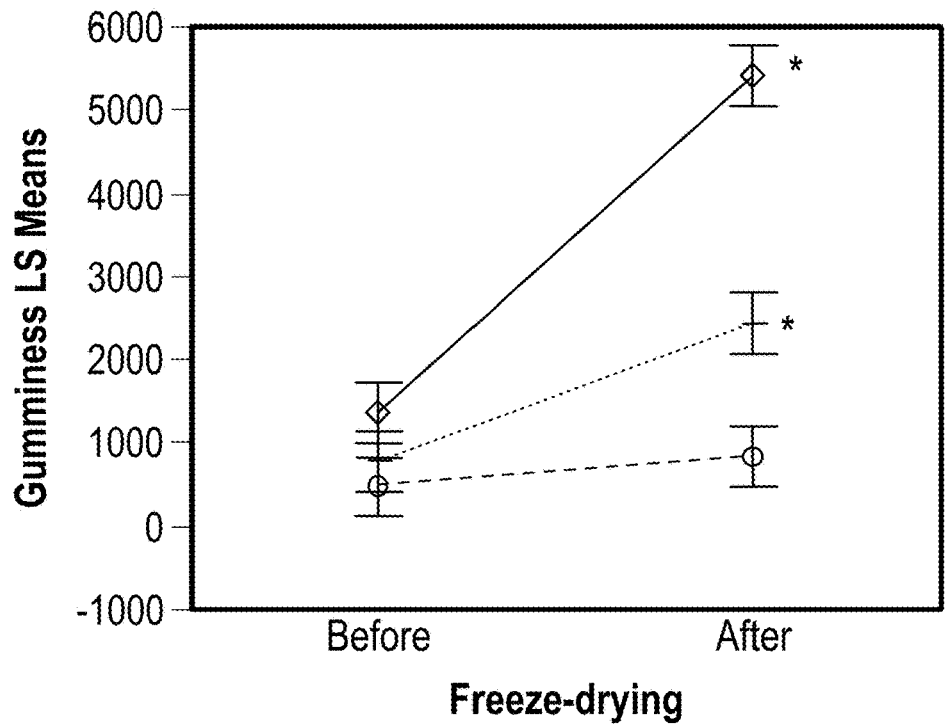
FIG. 5C shows a texture profile analysis, specifically looking at gumminess, of the 3D printed hydrogels before and after freeze-drying for the three optimal formulations in a least squares means plot. *: significant difference ($p<0.05$) was found within the same group before and after freeze-drying.
Figure 5D:
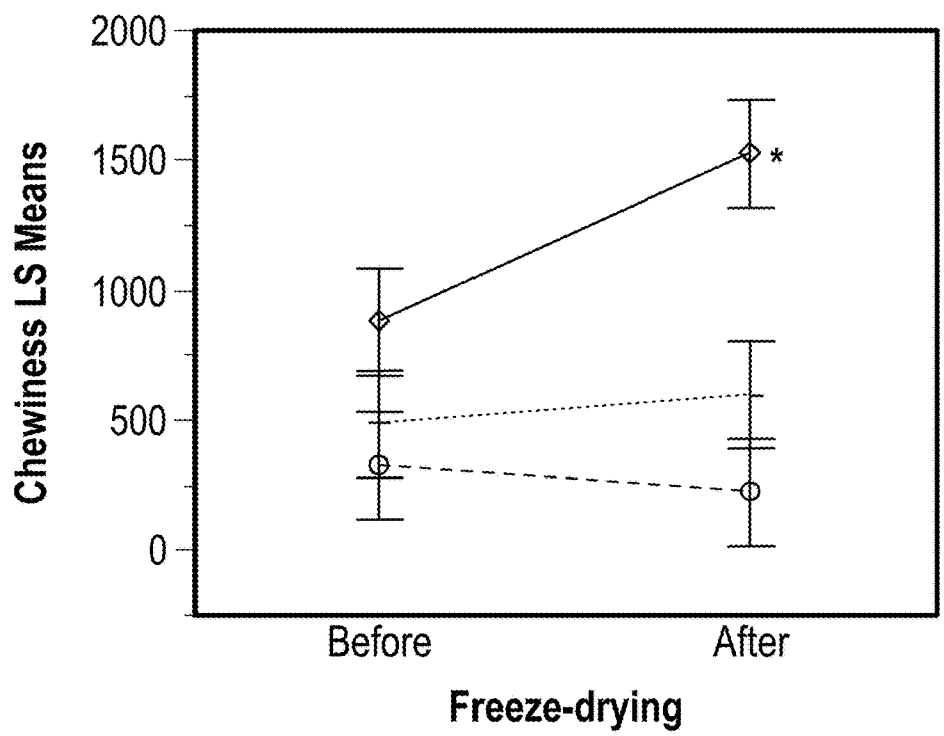
FIG. 5D shows a texture profile analysis, specifically looking at chewiness, of the 3D printed hydrogels before and after freeze-drying for the three optimal formulations in a least squares means plot. *: significant difference ($p<0.05$) was found within the same group before and after freeze-drying.

Microencapsulation is a technique that shields the active ingredients, for example, vitamins, minerals, bioactive compounds, or live microorganisms within another material, in order to keep the active ingredient stable from the surrounding environment (Sun et al., 2015). The microstructure of 3D printed objects was observed after freeze-drying by SEM (FIG. 4). Pure gelatin (FIGS. 4A-4C) exhibited a dendritic, fibrillated texture. The pores from a longitudinal section view had a diameter range from 70 to 350 µm. With a lower concentration of gelatin (3%), the structure displayed a more fragmented texture from the longitudinal section (FIG. 4A). On the other hand, pure alginate groups have a homogeneous morphology with a uniformly distribute circular hollows all over the longitudinal-section surface. As shown in FIGS. 4D-4F, the higher concentration of pure alginate resulted in a higher distribution of pores. Pore size dimension was around 95 µm for 3% of pure alginate (FIG. 4D), while 7% of pure alginate have smaller pore sizes ranging from 30 to 64 µm. More hollows were found with a lower concentration of pure alginate (3%), and the porosity, the empty space within the total space, was higher due to the higher water content, which was pulled away during the freeze-drying process. SEM images for the preferred formulations, 3% G/A 2:1, 5% G/A 1:1 and 7% G/A 1:2, were shown in FIGS. 4G-4I. The microstructure of the preferred formulations were SEM photomicrographs of 3% G/A 2:1 of gelatin-alginate hydrogel appeared to have higher porosity compared to 5% G/A 1:1 and 7% G/A 1:2 of a gelatin-alginate hydrogel. The porosity could serve as an ideal structure for cell infiltration and growth in addition to loading nutritional ingredients for further purposes. For example, the dimension for bacteria is usually ranges from 1 to 2 µm in length, thus it is possible for probiotics to be trapped inside the structure. The encapsulation method we are planning, is extrusion encapsulation. Typically, extrusion encapsulation is done by pre-mixing the active ingredients into the hydrogel, which is fabricated from biopolymers. As described in the previous study using probiotic as the active ingredient, the probiotic-loaded hydrogel was formed by three main steps: (1) pre-mix the probiotic into an aqueous biopolymer solution which will then be gelled; (2) extrude the bacteria-loaded biopolymer droplet into a gelling agent through a small nozzle; (3) stabilize the biopolymer droplets by gelation or coating methods.

Texture Profile Analysis

The texture profile analysis (TPA) attributes of four preferred formulations of the gelatin-alginate hybrid 3D printed hydrogels with 3% of pure gelatin, 3% G/A 2:1, 5% G/A 1:1, and 7% G/A 1:2, and commercial food products were shown in Table 3. Table 3 presents the TPA results of 3D printed hydrogel before freeze-drying versus commercial gummy supplement and hydrogel after freeze-drying versus the freeze-dried Yogurt Melts®. Among the preferred formulation for the printed hydrogel before freeze-drying, 7% G/A 1:2 has the largest hardness value of 2050.79 g, followed by 5% G/A 1:1, 3% G/A 2:1, with a value of 1286.16, and 727.45 g, respectively. The hardness of 7% G/A 1:2 is significantly higher than 3% G/A 2:1 ($p<0.05$). In conclusion, the hardness of a 3D printable material ranged from 727.45 to 2050.79 g. The adhesiveness value obtained from the preferred formulation of gelatin-alginate matrix were ranged from −237.29 to −694.81 g s. The highest value for adhesiveness was found in 7% of G/A 1:2, with a value of −694.81 g s. Whereas, 3% G/A 2:1 and 5% G/A 1:1 were given in a lower value of −237.29 and −389.36 g s, respectively. There were significant differences ($p<0.05$) in the adhesiveness between each group of the preferred formulations. Springiness is the degree to which the sample returns to its original height after compression, which could represent the perception of gel 'rubberiness" in the mouth. Gel with high springiness indicates that the structure is broken into few large pieces during the first compression, whereas gel with low springiness will result in structure breaking into many small pieces. However, no significant differences ($p>0.05$) were found between the three preferred formulations.

Cohesiveness can represent the extent to which the sample deforms when compressed. From Table 3, it is shown that the value of cohesiveness for three formulations range from 0.60 to 0.66, and there were no significant differences ($p>0.05$) between the three formulations. Furthermore, the gumminess, chewiness for the three preferred groups were not significantly different ($p>0.05$). When compared to the commercial gelatin-based gummies, the 3D printed objects showed significantly ($p<0.05$) low hardness, adhesiveness, springiness, cohesiveness, gumminess, chewiness, and resilience. Overall, the 3D printed drop shape objects fabricated with 7% G/A 1:2 showed the highest hardness and adhesiveness, among the three preferred formulations.

The bottom of Table 3 shows the TPA results for hydrogel after freeze-drying with preferred formulations and commercial freeze-dried product: Yogurt Melts®. Texture profile analysis of the 3D printed hydrogels with the optimal formulation: 3% G/A 2:1, 5% G/A 1:1 and 7% G/A 1:2, before and after freeze-drying were compared in the least squares means plot in FIG. 5. In general, significant differences were found in hardness, adhesiveness, gumminess, and chewiness, for each formulation before and after freeze-drying as shown in FIG. 5).

7% G/A 1:2 had the highest hardness value of 15,042.78 g among the three preferred formulations. The hardness significantly increases ($p<0.05$) as the total solid concentration increased. However, there were no significant differences in adhesiveness, springiness, cohesiveness and resilience for all three formulations. This may be due to the hard and dry texture of the freeze-dried hydrogel. After the first compression cycle, the freeze-dried hydrogels were compressed under a normal force and flatten into a small piece, and without the water content, the hydrogel does not present enough resilience for it to fight against to regain its original shape and size. Moreover, gumminess is the product of hardness and cohesiveness, as the total solid concentration increased, the gumminess increased significantly ($p<0.05$). The hardness of the commercial freeze-dried food product: Yogurt Melts® was significantly higher ($p<0.05$) than the freeze-dried hydrogel with all three preferred formulations, with a value of 20,359.51 g.

Conclusions

In this study, the suitable 3D printing materials were formulated with hybrid hydrogels prepared by different concentrations and ratios of gelatin and alginate. We have successfully fabricated the designed geometries, which simulated the shape of a snack food, i.e. chocolate drop. The preferred printing quality was observed for 3% G/A 2:1, 5% G/A 1:1, and 7% G/A1:2 hybrid hydrogels, which presented acceptable extrudability and shape retention performance. The suitable 3D printing hybrid gels exhibited shear-thinning behavior and a loss factor in the range of 0.48-0.58, during the frequency sweep of 15-40 rad/s, which is the corresponding frequency that can be related to our 3D printing settings. These rheological properties could be used as a criterion when determining the printability for a potential hydrogel-based material by the extrusion-based printer. Furthermore, the 3D printed matrices had shown relatively low hardness, springiness, cohesiveness, gumminess, and chewiness, compared to commercial gelatin-based gummies. To prevent shape deformation and to extend the shelf life, the 3D printed semi-solid objects were post-processed by freeze-drying, which resulted in a porous, low density, and crunchy matrix with low moisture content and water activity. Furthermore, the texture profile analysis on hardness also increased significantly after freeze-drying. These fabricated gel-based matrices could be potentially used as the delivery system to upload other bioactive components in the field of bioengineering, pharmaceutical, nutraceutical, and food industry.

TABLE 2

Estimated yield stress for 3%, 5%, and 7% of gelatin-alginate mixture with pure gelatin, pure alginate, G/A ratio 2:1, 1:1, and 1:2. Values are presented in mean ± standard deviation (n = 3); Values followed by different superscript are significantly different, $p < 0.05$.

|  | Pure Gelatin | Pure Alginate | G/A 2:1 | G/A 1:1 | G/A 1:2 |
| --- | --- | --- | --- | --- | --- |
| 3% | 85.37 ± 6.67$^g$ | 52.01 ± 0.75$^h$ | 79.37 ± 0.41$^g$ | 37.90 ± 0.58$^h$ | 26.60 ± 0.66$^h$ |
| 5% | 158.83 ± 1.31$^f$ | 229.77 ± 3.15$^d$ | 199.04 ± 3.16$^e$ | 197.73 ± 5.83$^e$ | 169.09 ± 1.72$^f$ |
| 7% | 439.69 ± 16.51$^c$ | 650.47 ± 7.93$^a$ | 419.03 ± 17.67$^c$ | 490.35 ± 17.29$^b$ | 502.34 ± 8.94$^b$ |

TABLE 3

Texture profile analysis of the 3D printed objects before and after freeze-drying: Hardness, adhesiveness, springiness cohesiveness, gumminess, chewiness, and resilience of the preferred concentration and G/A ratio of the material. Values are presented in mean ± standard deviation (n = 3); Values for a particular column followed by different superscript are significantly different, $p < 0.05$.

|  | Hardness (g) | Adhesiveness (g · s) | Springiness | Cohesiveness | Gumminess (g) | Chewiness (g) | Resilience |
|---|---|---|---|---|---|---|---|
| Non-Freeze Dried | | | | | | | |
| 3% G/A 2:1 | 727.45 ± 21.53$^c$ | −237.20 ± 12.23$^b$ | 0.68 ± 0.02$^b$ | 0.66 ± 0.03$^b$ | 481.38 ± 31.77$^b$ | 326.08 ± 29.38$^b$ | 0.06 ± 0.00$^c$ |
| 5% G/A 3:1 | 1286.16 ± 26.22$^{bc}$ | −389.36 ± 28.66$^c$ | 0.63 ± 0.06$^b$ | 0.60 ± 0.03$^b$ | 774.08 ± 36.59$^b$ | 487.45 ± 63.02$^b$ | 0.07 ± 0.00$^{bc}$ |
| 7% G/A 3:2 | 2050.79 ± 102.43$^b$ | −694.81 ± 41.65$^d$ | 0.65 ± 0.01$^b$ | 0.66 ± 0.02$^b$ | 1363.23 ± 106.66$^b$ | 880.86 ± 75.54$^b$ | 0.08 ± 0.00$^b$ |
| Commercial gummy | 26,033.14 ± 933.41$^a$ | −0.44 ± 0.23$^a$ | 0.92 ± 0.06$^a$ | 0.89 ± 0.04$^a$ | 23,174.42 ± 1449.47$^a$ | 21,397.50 ± 2734.34$^a$ | 0.50 ± 0.01$^c$ |
| Freeze Dried | | | | | | | |
| 3% G/A 2:1 | 2754.29 ± 13.44$^d$ | 0.00 ± 0.00$^a$ | 0.27 ± 0.03$^{ab}$ | 0.30 ± 0.02$^a$ | 835.21 ± 69.99$^c$ | 226.37 ± 42.86$^b$ | 0.09 ± 0.00$^b$ |
| 5% G/A 1:1 | 7613.93 ± 225.62$^c$ | −0.65 ± 0.83$^a$ | 0.24 ± 0.08$^{ab}$ | 0.32 ± 0.04$^a$ | 2436.99 ± 327.58$^b$ | 596.39 ± 296.38$^b$ | 0.11 ± 0.01$^{ab}$ |
| 7% G/A 1:2 | 15,042.78 ± 1845.75$^b$ | −0.47 ± 0.64$^a$ | 0.28 ± 0.02$^a$ | 0.36 ± 0.01$^a$ | 5411.82 ± 594.44$^a$ | 1525.69 ± 243.16$^a$ | 0.14 ± 0.00$^{ab}$ |
| Yogurt Melt® | 20,359.51 ± 986.85$^a$ | −0.36 ± 0.22$^a$ | 0.13 ± 0.06$^b$ | 0.17 ± 0.02$^b$ | 3435.60 ± 534.63$^b$ | 477.08 ± 263.80$^b$ | 0.12 ± 0.02$^a$ |

TABLE 4

Moisture content and water activity of preferred gelatin-alginate bio-ink formulations: 3% G/A 2:1, 5% G/A 1:1 and 7% G/A 1:2 before and after freeze-drying. Values are presented in mean ± standard deviation (n = 3). Values followed by different superscript are significantly different, $p < 0.05$.

|  | Moisture content (wt %) | | Water Activity | |
|---|---|---|---|---|
|  | Before | After | Before | After |
| 3% G/A 2:1 | 97.23 ± 0.07$^a$ | 3.76 ± 0.88$^{de}$ | 0.99 ± 0.00$^A$ | 0.56 ± 0.02$^B$ |
| 5% G/A 1:1 | 95.92 ± 0.03$^b$ | 4.27 ± 0.62$^d$ | 0.98 ± 0.00$^A$ | 0.53 ± 0.01$^{BC}$ |
| 7% G/A 1:2 | 93.91 ± 0.02$^c$ | 3.03 ± 0.16$^e$ | 0.99 ± 0.00$^A$ | 0.51 ± 0.03$^C$ |

Example 2

In this Example, the aim was to integrate manufacturing methods of encapsulation, 3D printing, and freeze-drying to fabricate shelf-stable, food-grade gelatin-alginate hydrogels that can carry and deliver probiotics effectively. We hypothesize that the gelatin-alginate hydrogel can serve as a delivery system for *B. lactis* and *L. acidophilus*, and the cell viability can maintain at least $10^6$ CFU/g after the integrated processes consisting of encapsulation, 3D printing, and freeze-drying.

Materials and Methods

Hydrogel Sample Preparation

Hybrid hydrogels were prepared from food-grade biopolymers: Type-B gelatin (bovine) donated from Sigma-Aldrich (St. Louis, MO) and sodium alginate (TICA-algin 400 Powder) donated by TIC Gums (White Marsh, MD). Based on the previous study (Kuo et al., 2021), the three preferred hydrogel formulations for the extrusion-based 3D printing platform were: 3% G/A 2:1, 5% G/A 1:1, and 7% G/A 1:2, presented in the percentage of the total solid content (w/w %) followed by the ratio (G/A) of gelatin and alginate (w/w). First, the gelatin particles and alginate powder were weighed to their designated amounts and mixed with sterile deionized (DI) water in a sterile flask. The hydrogel mixture was manually stirred while heated at 60° C. to 70° C. until the particles were fully dissolved and homogenized. The solutions were then cooled down in a 40° C. water bath and were ready for the encapsulation of probiotics.

Probiotics Preparation and Encapsulation

Two commercial probiotics strains were used in this study: *Bifidobacterium lactis* (HOWARU® Bifidous) and *Lactobacillus acidophilus* (HOWARU® Dophilus), which were kindly donated by Danisco (Dupont™ Danisco USA Inc). The de Man Rogosa Sharpe (MRS) broth and MRS agar were purchased from Oxoid (Oxoid, Basingstoke, UK).

All the growth media and supplements were sterilized at 121° C. for 15 minutes in an autoclave (Model: ES-315, TOMY Digital Biology Co., Ltd, Tokyo, Japan) and the L-cysteine solution was filtered through a Durapore® Hydrophilic Polyvinylidene Fluoride (PVDF) syringe membrane (MilliporeSigma™, Burlington, MA) before use. One gram of the lyophilized culture was inoculated in the 49 ml sterilized MRS broth medium and then incubated anaerobically for 24 h at 37° C. Next, the broth culture of each probiotic was centrifuged at 5000 rpm for 15 mins, washed twice with refrigerated 0.1% peptone diluent, and then centrifuged again at 5000 rpm for 30 min. Subsequently, the supernatant was removed, and a portion of the DI water for making the gelatin-alginate hydrogel solution was used to resuspend the cell pellets.

After the cell pellets were collected, it was transferred and encapsulated into the pre-mix hydrogel solution and gently mixed until homogenized, to make a final weight of 50 g. After encapsulation, the probiotic-containing gelatin-alginate hydrogels were centrifuged at 3000 rpm for 2 min to remove the air bubbles and transferred to sterile syringe tubes, which function as the paste extruder for extrusion-based 3D printer. All gelatin-alginate hydrogels encapsulated with probiotics were set at room temperature for the 24 h gelation process.

Rheological Properties

The rheological properties of the probiotic-containing hydrogels were characterized by Discovery HR-2 Rheometer (TA Instruments, New Castle, DE), using a 40 mm diameter, 2° cone-plate geometry with the gap of 1000 μm. The methodology was followed by our previous study (Kuo et al., 2021). All measurements were carried out at 20° C. Before each measurement, the excess hydrogels were scraped out, and a 10 sec of soaking time was applied to reach the steady-state. The flow behavior and viscosity were measured by the flow ramp test, with the shear rate increasing from 0.1 to 30.0 $s^{-1}$. Linear viscoelastic region (LVR) was determined by amplitude stress sweep test at a fixed frequency of 1.0 Hz with the oscillation strain range from 1 to 1000% in log mode. In the LVR, the storage modulus is independent of strain. The estimated yield stress was determined by the point where the storage modulus G' dropped from the stress plateaus in the log-log plot, which can also be considered as the critical stress where the structure breakdown occurs. Finally, the oscillation frequency sweep test was used to determine the dynamic modulus: storage modulus (G'), loss modulus (G"), and loss factor tan δ (G"/G'). Angular frequency of 0.1 to 100 rad/s was set for the frequency sweep test in a logarithmic sweep mode at a constant deformation strain of 0.029.

3D Printing and Freeze-Drying

The customized 3D printer driven by a stepper motor described in the previous study was used in this study (Cheng, Y., et al., 2020, 3D printing of extended-release tablets of theophylline using hydroxypropyl methylcellulose (HPMC) hydrogels. International Journal of Pharmaceutics, 591 (October), 119983. https://doi.org/10.1016/j.ijpharm.2020.119983, herein incorporated in its entirety by reference). All of the 3D printing processes were performed at room temperature. The Velleman K8200 printer (Velleman Inc., Fort Worth, TX), coupled with an extrusion-based syringe driven by pressurized air was used. Nozzle diameter was 0.636 mm. The sterile syringe was loaded with the probiotic-containing hydrogel, which had set for 24 h beforehand. The 3D printing process was controlled by Repetier-Host software V2.1.6 (Hot-World GmbH & Co. KG, Willich, Germany), and the parameters were set as 8.00 mm/s of printing speed with a 100 mm3/s of feed rate. The geometry was designed into a chocolate drop shape (L×W×H=16×16×9.7 mm) and was sliced into layers by an open-source Slic3r software with a total number of layers were 11. A concentric infilled pattern was designed for the printing process, and it took within 4 min to complete each tablet. After 3D printing, the hydrogel tablets were post-processed with freeze-drying. All samples were frozen in a freezer (−30° C.) before placing into the freeze-dryer. Freeze-drying processing was carried out with a pilot freeze-dryer (Virtis Genesis SQ freeze dryer) under a chamber pressure below 26.66 kPa for approximately 24 h.

Texture Profile Analysis and Physicochemical Properties

Texture profile analysis was carried out using the TA.XT plusC texture analyzer (Texture Technologies Corp. and Stable Micro Systems, Ltd Hamilton, MA). The two sequential compression test was conducted for both the hydrogels before and after freeze-drying under ambient temperature. An acrylic cylindrical plate probe with a 35-mm diameter was attached to the texture analyzer. The samples were compressed to 80% of strain deformation with a trigger force of 10 g. The compression rate was set as 1.0 mm/s, and the pre-test speed and post-test speed was 1.5 mm/s. There was a delay time of 5 seconds between the two compression cycles.

Water activity ($a_w$) of the hydrogels before and after 3D printing were measured by AQUALAB 4TE water activity meter (Decagon Devices, Pullman, WA) at 25° C.

Determination of Probiotics Viability

The viability of L. acidophilus and B. lactis were carried out by the pour plate technique at four timepoints: initial, after encapsulation, after 3D printing, and after freeze-drying. The initial was the probiotic cells collected after the centrifugation of the original broth culture. After encapsulation and gelation, ten grams of the original G/A hydrogel were transferred into a sterile blender bag, and then 90 ml of sterilized 0.1% peptone diluent (room temperature) was added. The hydrogel and diluent were homogenized manually until the hydrogel dissolved completely. After 3D printing and after freeze-drying, one hydrogel tablet (approximately one gram on a wet basis), either in 3D printed form or freeze-dried form, was placed into a sterile blender bag, and 99 ml of sterilized 0.1% peptone diluent was added. One mL of the solution was transferred into a 96-well plate and then serial diluted. After serial dilution, 100 μL of the solution was subsequently plated by the pour plate technique onto the MRS agar (Oxoid, Basingstoke, UK). MRS agar for L. acidophilus was supplemented with 0.5% (w/v) lactose solution, whereas 0.05% (w/v) of L-cysteine solution was supplemented for B. lactis. Duplicate plates for each dilution were incubated at 37° C., for 72 h (L. acidophilus) and 48 h (B. lactis) under anaerobic conditions, which was done by using the BD GasPak™ EZ Anaerobe Container Systems (Becton, Dickinson and Company, Franklin Lakes, NJ). The suitable colony counting range was within 25-250 CFU/plate. Probiotic viability was enumerated as colony-forming units per gram of the sample and presented as log CFU/g. Freeze-dried hydrogels encapsulated with B. lactis and L. acidophilus were store at room temperature for up to 12 weeks and 4 weeks, respectively. The viable cell counts were obtained according to the previous method above. Results were presented as log CFU/g.

Probiotics Viability During Storage

The final freeze-dried products loaded with probiotics was placed in petri dish and wrapped with Petrifilm™. The products were stored at room temperature for up to 12 weeks, until the viability of loaded probiotics reduced to <$10^5$ CFU/g. Viability was analyzed as explained above.

Statistical Analysis

Three batches were conducted for the viability of B. lactis and two for L. acidophilus. Measurements of rheological properties, water activity, and texture profile analysis were performed in triplicate. Data were statically analyzed with JMP Pro 14 (SAS Institute Inc., Cary, NC). The significant difference between means was determined by one-way analysis of variance and Tukey's HSD (Honestly Significant Difference) test with a significance level of p<0.05.

Results and Discussion

Rheological Properties of Hydrogel

Figure 6A:
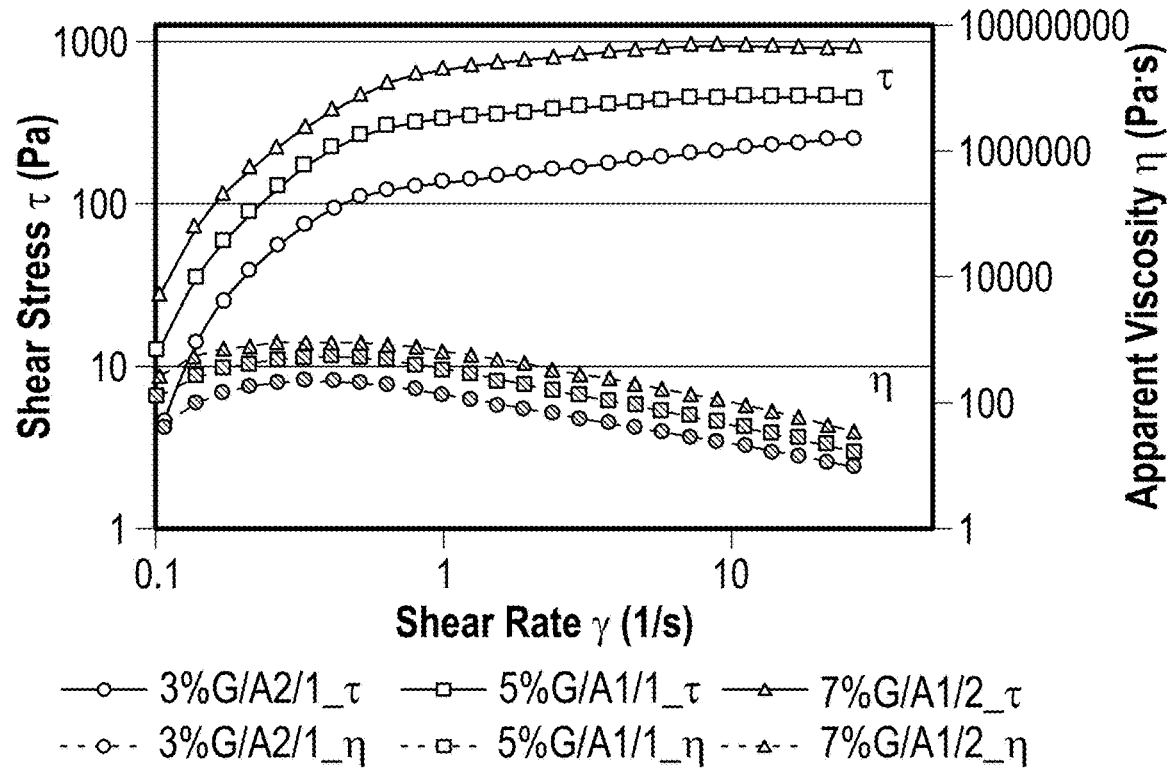
FIG. 6A shows shear stress ($\tau$) and apparent viscosity ($\eta$) as a function of shear rate ($\dot{\gamma}$) for 3% G/A 2:1, 5% G/A 1:1, and 7% G/A 1:2 without *B. lactis* and *L. acidophilus*. Data points represent mean with error bars denoted as standard error bars of three replicates.
Figure 6B:
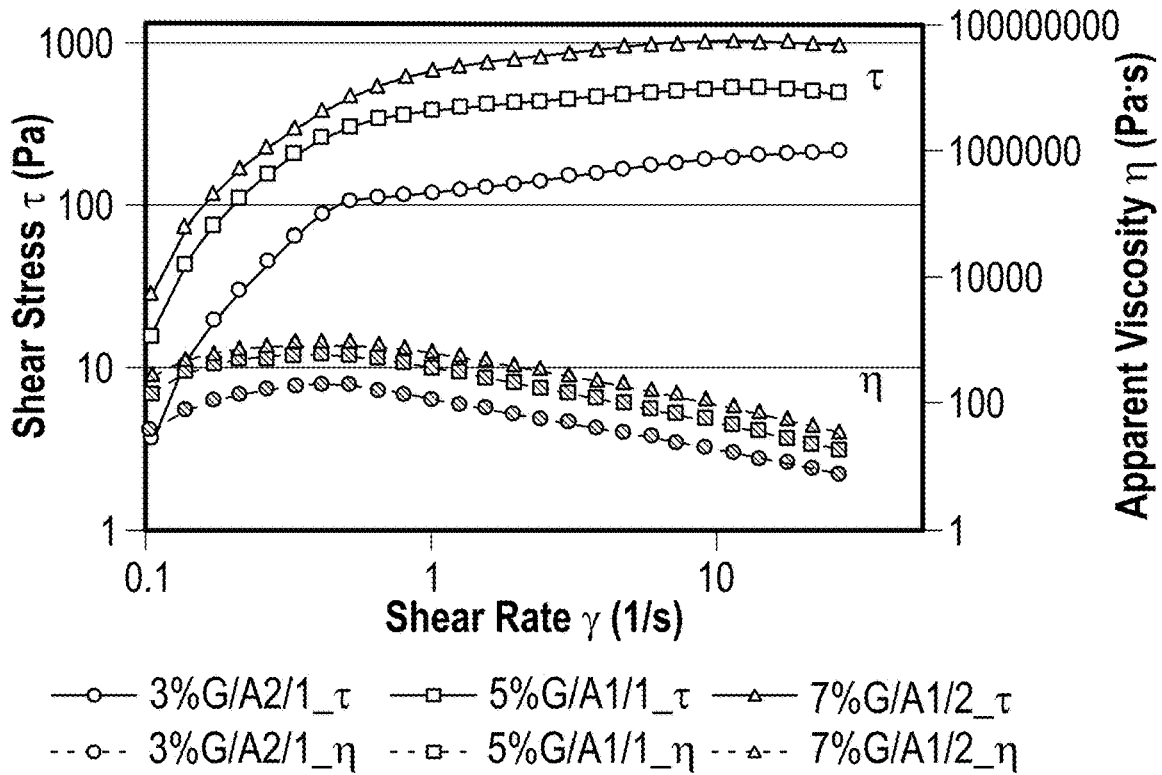
FIG. 6B shows shear stress ($\tau$) and apparent viscosity ($\eta$) as a function of shear rate ($\dot{\gamma}$) for 3% G/A 2:1, 5% G/A 1:1, and 7% G/A 1:2 with *B. lactis*. Data points represent mean with error bars denoted as standard error bars of three replicates.
Figure 6C:
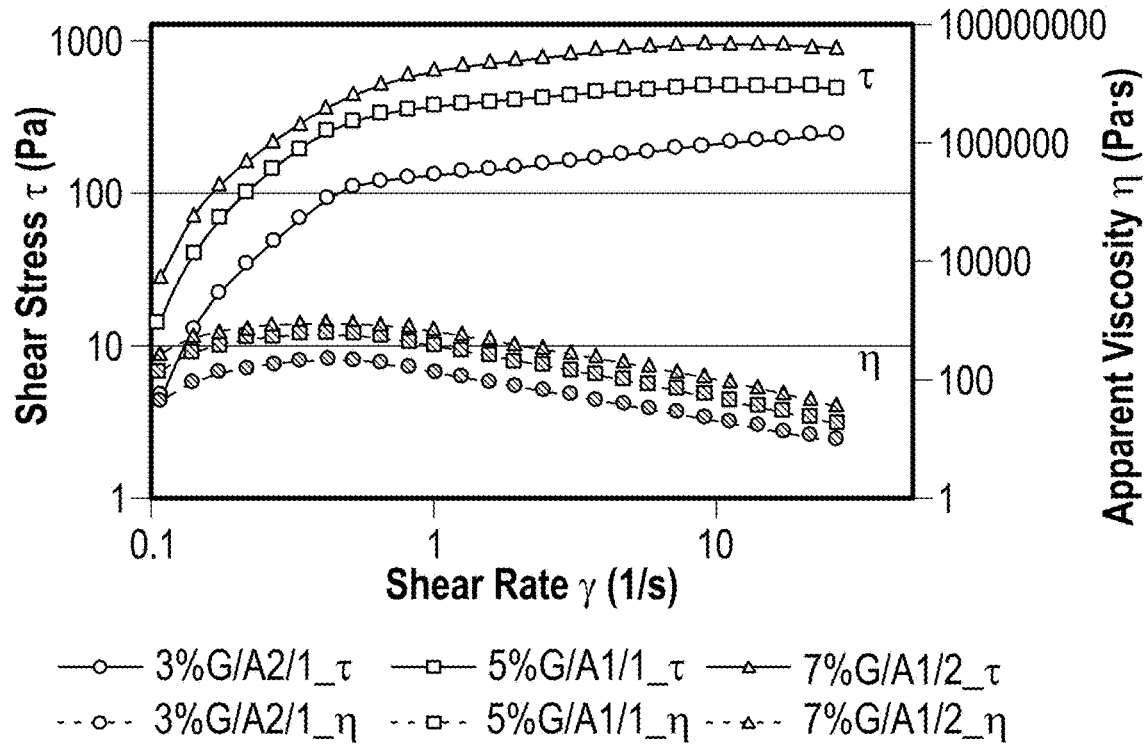
FIG. 6C shows shear stress ($\tau$) and apparent viscosity ($\eta$) as a function of shear rate ($\gamma$) for 3% G/A 2:1, 5% G/A 1:1, and 7% G/A 1:2 with *L. acidophilus*. Data points represent mean with error bars denoted as standard error bars of three replicates.

Rheological tests were conducted to determine the printability of gelatin-alginate (G/A) hydrogels for extrusion-based 3D printing. In Example 1, it was shown that hydrogels made with 3% G/A 2:1, 5% G/A 1:1, and 7% G/A 1:2 were the preferred formulations among all nine combinations of the total solids content of 3%, 5%, and 7% with G/A ratio of 2:1, 1:1, and 1:2. Here, we further investigated the rheological properties of the G/A hydrogels encapsulated with the two probiotics *B. lactis* and *L. acidophilus*. Flow behavior and apparent viscosity of the hydrogels are shown in FIGS. 6A-6C. Shear-thinning behavior, also known as pseudoplastic behavior, was observed for all three preferred formulations. The apparent viscosity decreased with the increase in shear rate. No significant differences were found in the flow behavior between with and without encapsulation of *B. lactis* and *L. acidophilus* (p>0.05). The effect of total solids content on apparent viscosity was significant (p<0.05). When under the same shear rate, the apparent viscosity and stress increased significantly as the total solids concentration of the hydrogels increased. The apparent viscosity for 7% G/A 2:1 was significantly higher than 5% G/A 1:1 followed by 3% G/A 2:1. Materials presenting higher apparent viscosity hold higher viscosity between the printed filaments, which results in better shape retention after deposition. A hydrogel material is considered printable when a low viscosity is presented as shear stress is applied, and the viscosity should recover quickly after the shear stress is removed. Based on this shear-thinning behavior and the post-printing stability, the preferred formulations are suitable for extrusion-based 3D printing, with or without probiotics.

Yield stress is the minimum stress/force needed to allow the materials to flow. During the 3D printing process, a larger-than-yield stress external force is required so that the printing material can be extruded continuously through the nozzle. The estimated yield stress for the three preferred formulations is shown in Table 5. Without encapsulation, when the total solids concentration increased, the estimated yield stress increased significantly. The same trend was discovered in the after-encapsulation group of *B. lactis* and *L. acidophilus* as well. The higher mechanical strength is likely due to more biopolymers being available for denser cross-linked network. However, in 3% G/A 2:1 and 7% G/A 1:2, the yield stress values were significantly different between without encapsulation, encapsulated with *B. lactis*, and encapsulated with *L. acidophilus*. There were no significant differences between without encapsulation and encapsulated with *L. acidophilus* in 5% G/A 1:2. Generally, these G/A hydrogels encapsulated with bacteria demonstrated lower yield stress values than without probiotics (Table 5). With these bacteria-loaded, G/A hydrogels composites, the bacteria cells were considered as the filler material whereas the G/A hydrogels were the matrix. According to the rule of mixture, the properties of a composite mixture are given by the weighted mean of the properties of matrix and filler material (Gooch, 2011).

Figure 7A:
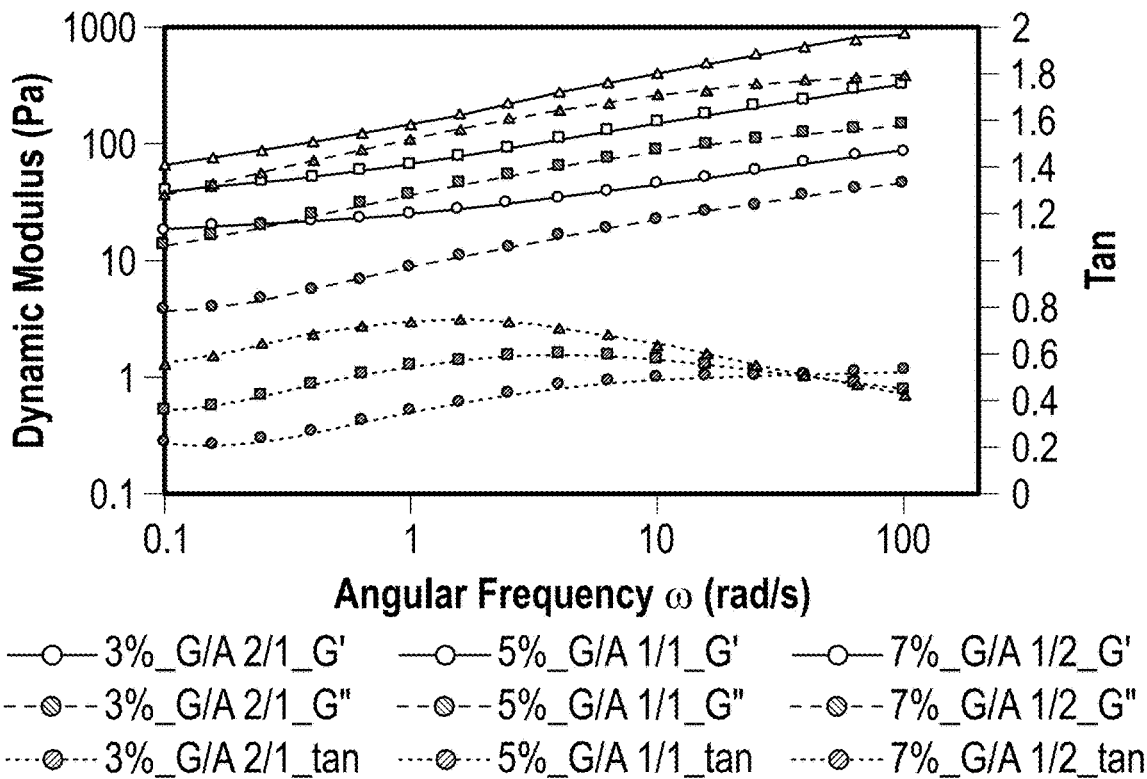
FIG. 7A shows the oscillation frequency sweep test without *B. lactis* and *L. acidophilus*: storage modulus (G'), loss modulus (G") and loss factor ($\delta$) as a function of angular frequency for 3% G/A 2:1, 5% G/A 1:1, and 7% G/A 1:2. Data points represent mean with error bars denoted as standard errors of three replicates.
Figure 7B:
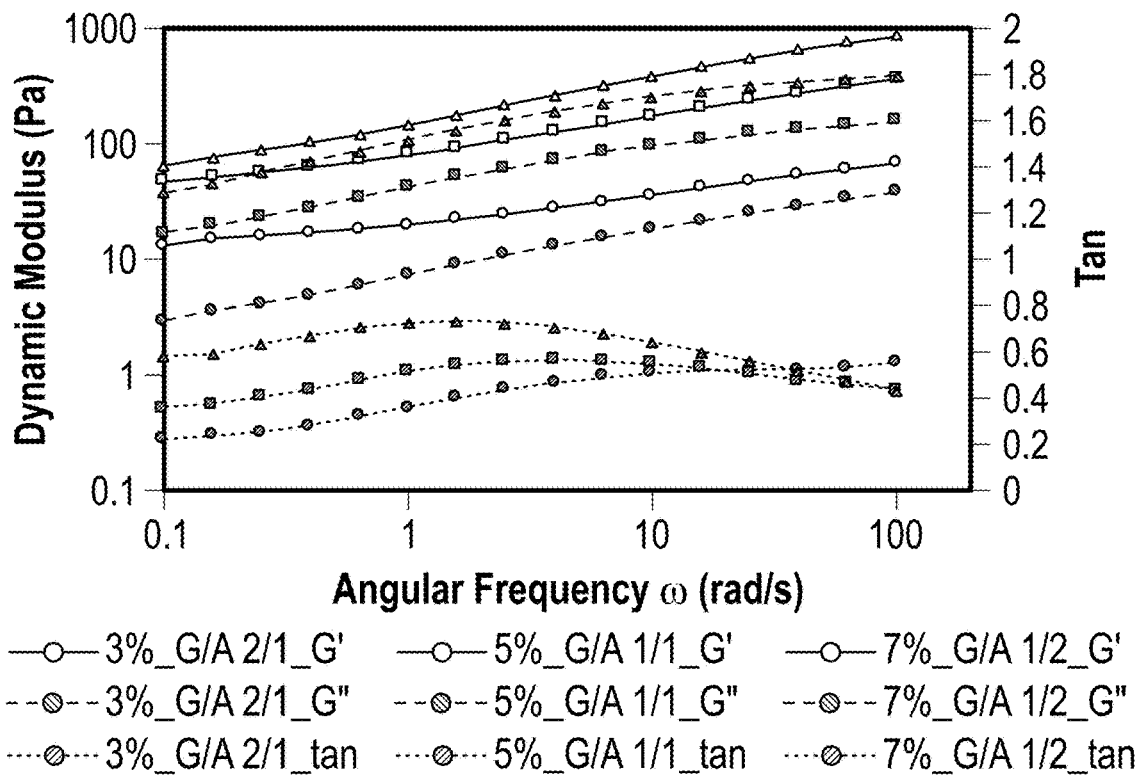
FIG. 7B shows the oscillation frequency sweep test with *B. lactis*: storage modulus (G'), loss modulus (G") and loss factor ($\delta$) as a function of angular frequency for 3% G/A 2:1, 5% G/A 1:1, and 7% G/A 1:2. Data points represent mean with error bars denoted as standard errors of three replicates.
Figure 7C:
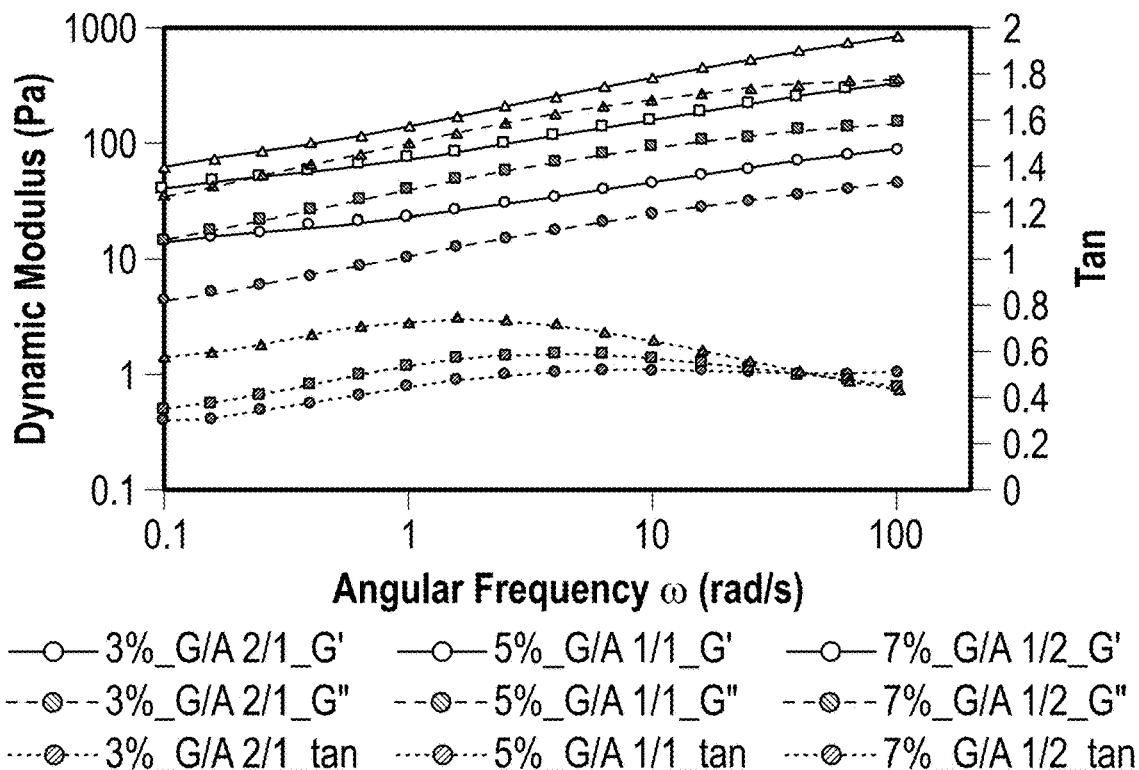
FIG. 7C shows the oscillation frequency sweep test with *L. acidophilus*: storage modulus (G'), loss modulus (G") and loss factor ($\delta$) as a function of angular frequency for 3% G/A 2:1, 5% G/A 1:1, and 7% G/A 1:2. Data points represent mean with error bars denoted as standard errors of three replicates.

Viscoelasticity is used to describe a material establishing both viscous and elastic characteristics under shear stress. Dynamic modulus: storage modulus (G') and loss modulus (G") and loss factor (tangent $\delta$=G"/G') as a function of angular frequency are presented in FIG. 7. For all three G/A formulations, storage modulus (G') was always larger than loss modulus (G"), indicating that the hydrogels were more solid-like. No significant difference was found between 3% G/A 2:1 and 5% G/A 1:1 in G' and G". However, when the total solids content increased to 7%, with G/A 1:2, it resulted in a significant increase in G' and G" in the dynamic oscillation measurements. No significant difference in the dynamic modulus and loss factor was found among the hydrogels with and without encapsulation of probiotics. Under the frequency sweep of 15-40 rad/s, which was the corresponding frequency related to our 3D printing setting, the loss factors ($\delta$) for the three preferred formulations of 3% G/A 2:1, 5% G/A 1:1, and 7% G/A 1:2 were in the range of 0.48 to 0.61 This result is similar to a previous study, in which they found hydrogels composite with gelatin and alginate exhibited an excellent extrusion uniformity with a loss tangent range between 0.25 to 0.45. However, they concluded that the materials outside the boundaries may still be printable under different settings, dependent on applications. Overall, there is no significant difference in hydrogels' viscoelasticity with and without loaded cells at approximately $10^9$ CFU/g.

The three preferred formulations of G/A hydrogels were considered printable due to the following characteristic: (1) they can be continuously extruded out through the nozzle by a given pressure; (2) during the layer-by-layer depositing process, the filaments were uniform, and the dimension of the designed shape was consistent; (3) finally, once being printed, they possessed sufficient strength to support their own weight while minimizing deformation. Adding gelatin to alginate to form a bio-ink mixture showed better printability by increasing the viscosity and fixing the 3D structure of the printed shape during the 3D printing process.

3D Printing and Freeze-Drying

Representative images of the 3D printed semi-solid objects with *B. lactis* and *L. acidophilus* before and after freeze-drying are presented in FIGS. 8A-8R. Visually, the 3D printed hydrogels without bacteria (FIGS. 8A, 8D, and 8G), with *B. lactis* (FIGS. 8B, 8E, and 8H), and *L. acidophilus* (FIGS. 8C, 8F, and 8I) had similar shapes and surface roughness. Compared to the controls without loaded bacteria, the 3D-printed gels with live cells were more opaque and less transparent. However, there were slight differences among the three preferred 3D printed G/A hydrogels. Hydrogels made with the formulation of 3% G/A 2:1, which had the lowest total biopolymer content, demonstrated a wider shape in L (cm) and W (cm) (*B. lactis*: L=1.78±0.04 cm×W=1.78±0.03 cm; *L. acidophilus*: L=1.69±0.03 cm×W=1.70±0.01 cm) at the bottom (FIGS. 8B and 8C). Moreover, the height (*B. lactis*: H=0.90±0.03 cm; *L. acidophilus*: H=0.91±0.02 cm) and the resolution were the lowest among the other formulations. This was because of the diffusion of hydrogels due to gravity and the fusion effect during the printing process, which affect the printing resolution. Hydrogels with 3% G/A 2:1 had the largest moisture content (Table 9), and the weaker shape retention ability made it flatten. The geometries of 3D printed hydrogels made with 5% G/A 1:1 and 7% G/A 1:2 showed higher shape fidelity to our design, which was 16 mm in diameter and 9.7 mm in height.

Post-processing with freeze-drying has been shown to improve the mechanical strength of the 3D printed bioscaffold and present higher porosity. For food production, freeze-drying is a method of dehydration to extend shelf life without compromising the food quality. Food products are allowed to maintain their unique attributes such as flavors, colors, texture, and appearance by freeze-drying. FIGS. 8J-8R shows the images of G/A 3D printed hydrogels after post-processing with freeze-drying. There was some shrinkage across the 3D printed G/A hydrogel scaffolds along X, Y, and Z-axes after freeze-drying, especially for the 3% G/A 2:1 hydrogels (FIGS. 8J-8L). The reason is very likely due to the diffusion from gravity and the fusion progress of two adjacent printed layers of the hydrogels after 3D printing. Since it takes time for the 3D printed hydrogels to be completely frozen in the freezer, the above condition could take place much faster before solidification could happen. In contrast, hydrogels prepared with 5% G/A 1:1 (FIGS. 8M-8O) and 7% G/A 1:2 (FIGS. 8P-8R) established relatively high shape fidelity and retention. However, the surface smoothness was lower, where the layer-by-layer deposition could be seen clearly from the images.

As expected, water activity dropped significantly from values larger than 0.99 to values below 0.1 after freeze-drying (Table 6). Moisture content and water activity are critical factors that affect the stability of probiotic bacteria during storage. Generally, a low water activity value is better for dried probiotic bacteria preservation. During the storage period at room temperature, a low $a_w$ of 0.07 has been shown to improve bacterial survival within biopolymer gels. A previous study showed that L. acidophilus (La-5) freeze-dried in sucrose and lactose established a relatively higher relative survival rate at a low $a_w$ value of 0.11 compared with higher $a_w$ value of 0.43 during storage at 20° C. Another study suggested a value of 0.2 $a_w$ was appropriate for long-term storage for Bifidobacterium BB-12 encapsulated within alginate microcapsules followed by freeze-drying. With the low $a_w$ values, we expected the selected probiotic microorganisms to be stable within the freeze-dried 3D printed G/A hydrogels, where little free water was available for the biochemical reactions.

Viability of B. lactis and L. acidophilus

Figure 9A:
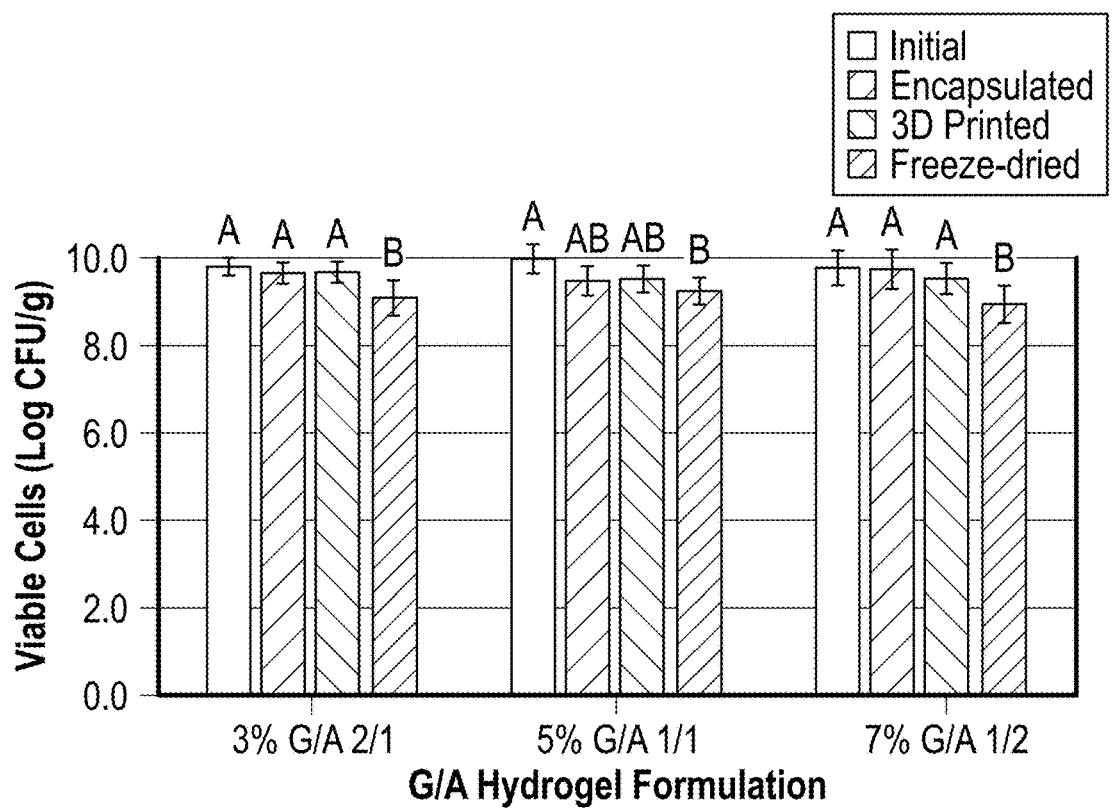
FIG. 9A shows the viability of *B. lactis* after manufacturing process of encapsulation, 3D printing, and freeze-drying within the gelatin-alginate (G/A) hydrogels with formulations of 3% G/A 2:1, 5% G/A 1:1, and 7% G/A 1:2. Bars with different letters are significantly different ($p<0.05$). Means values were obtained in triplicate for *B. lactis* and duplicate for *L. acidophilus*, and each sample was plated in duplicate.
Figure 9B:
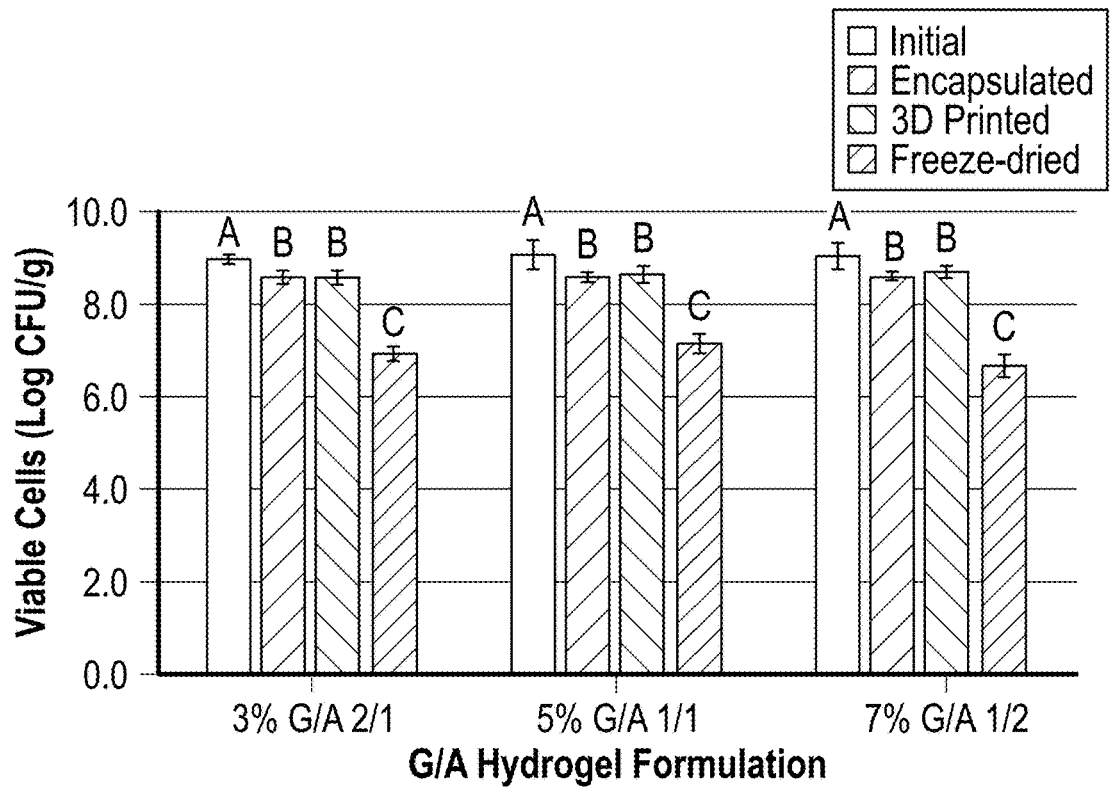
FIG. 9B shows the viability of *L. acidophilus* after manufacturing process of encapsulation, 3D printing, and freeze-drying within the gelatin-alginate (G/A) hydrogels with formulations of 3% G/A 2:1, 5% G/A 1:1, and 7% G/A 1:2. Bars with different letters are significantly different ($p<0.05$). Means values were obtained in triplicate for *B. lactis* and duplicate for *L. acidophilus*, and each sample was plated in duplicate.

FIGS. 9A and 9B show the effect of the integrated manufacturing of encapsulation, 3D printing, and freeze-drying on the viability of B. lactis and L. acidophilus. The initial viable cell counts were approximately 10 log CFU/g for B. lactis and 9 log CFU/g L. acidophilus. As shown in FIG. 9A, no significant reduction of viable cell counts was found between the encapsulated group and the 3D printed group for B. lactis among the three preferred gelatin-alginate (G/A) hydrogels. This means that the live cells of B. lactis were able to resist the stress from the encapsulation and 3D printing processes. Although a significantly lower number of viable cell counts were discovered after freeze-drying ($p<0.05$), the viable cell counts of B. lactis still exceeded 9 log CFU/g, and after the whole manufacturing process of encapsulation, 3D printing, and freeze-drying, there was less than 1 log reduction in the viability of B. lactis. No significant difference among the three preferred G/A hydrogel formulations was found after each manufacturing process.

The viability of L. acidophilus is presented in FIG. 9B. Unlike B. lactis, the viable cell counts for L. acidophilus significantly dropped from the initial 9.1 log CFU/g to around 8.7 log CFU/g for the encapsulated groups ($p<0.05$). This trend was the same for all three G/A hydrogels. Moreover, there was no significant difference between encapsulated and 3D printed groups among the three preferred G/A hydrogels. The viable cell counts for L. acidophilus decreased significantly in the freeze-dried groups with numbers of 7.0 log CFU/g for 3% G/A 2:1, 7.2 log CFU/g for 5% G/A 1:1, and 6.7 log CFU/g for 7% G/A 1:2. ($p<0.05$). Although an approximate 2 log reduction of viable cell counts was found in L. acidophilus, the levels were still above 6 log CFU/g, which meets the requirement of minimal live bacteria in probiotic food products.

Figure 10A:
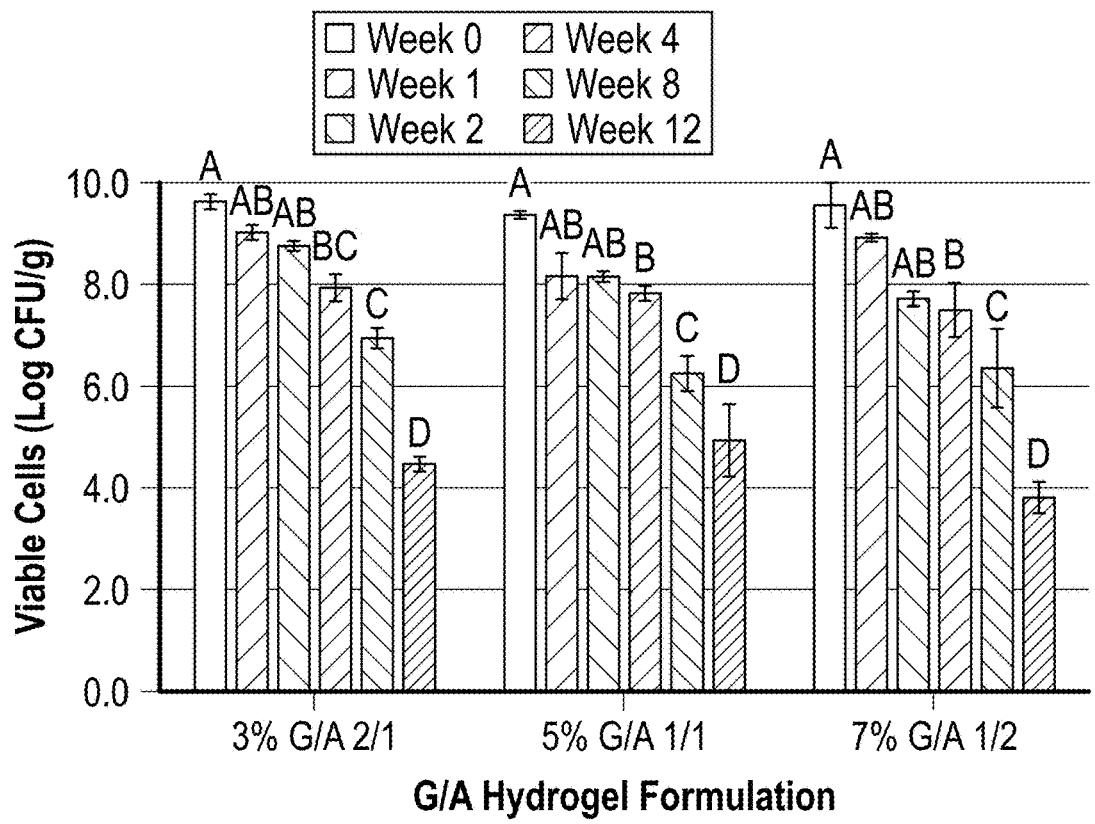
FIG. 10A shows the viability of *B. lactis* within the gelatin-alginate (G/A) hydrogels with formulations of 3% G/A 2:1, 5% G/A 1:1, and 7% G/A 1:2 during 12 weeks and 4 weeks of storage. Means values were obtained in duplicate, and each sample was plated in duplicate.
Figure 10B:
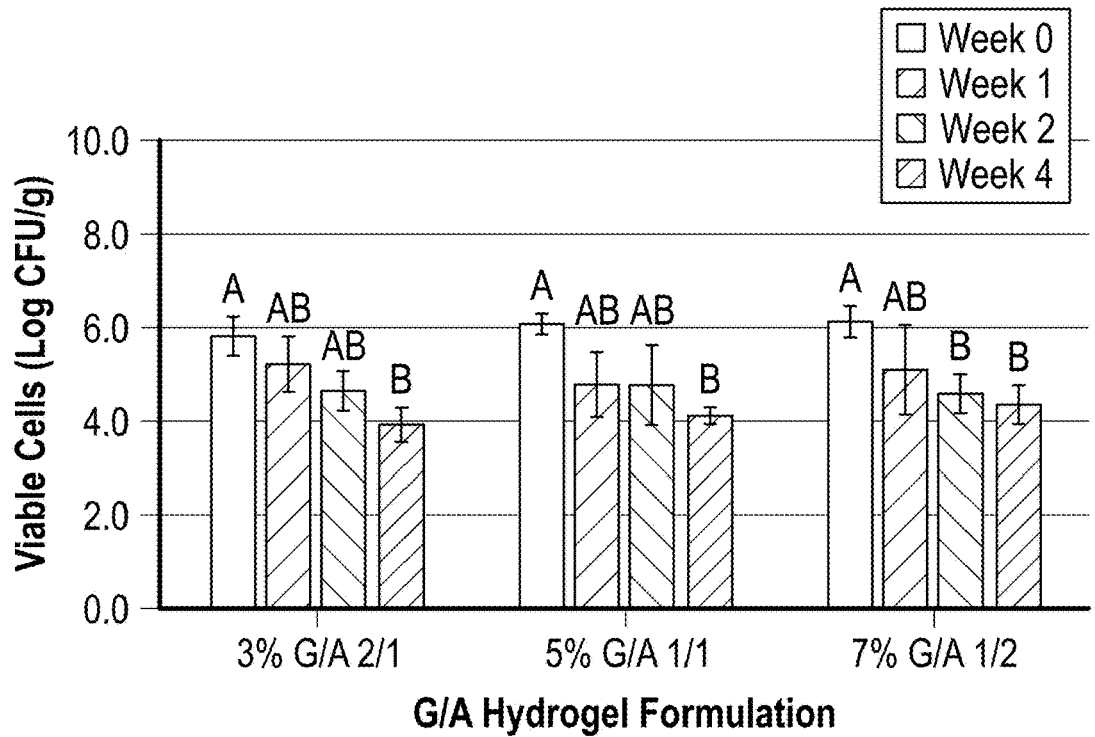
FIG. 10B shows the viability of *L. acidophilus* within the gelatin-alginate (G/A) hydrogels with formulations of 3% G/A 2:1, 5% G/A 1:1, and 7% G/A 1:2 during 12 weeks and 4 weeks of storage. Means values were obtained in duplicate, and each sample was plated in duplicate.

In general, B. lactis showed a better viability than L. acidophilus, upon the storage of 4 weeks (FIGS. 10A and 10B). No significant difference in the viability was found among the three G/A hydrogel formulations. The viable cell counts for B. lactis (FIG. 10A) were maintained at above 6 log CFU/g at week 8, with 7.0 log CFU/g for 3% G/A 2:1, 6.3 log CFU/g for 5% G/A 1:1, and 6.4 log CFU/g for 7% G/A 1:2. However, the viable cell counts for B. lactis at week 12 dropped significantly below 5 log CFU/g, indicating the end if shelf life based on the limit we set ($>10^6$ CFU/g). On the other hand, there was a significant decrease in the viable cell counts for L. acidophilus (FIG. 10B) between week 0 and week 4. The viable cell counts for L. acidophilus dropped below 5 log CFU/g at week 4. It is suggested that L. acidophilus may be more sensitive to the environment. Future work should be conducted to improve the viability of L. acidophilus. For example, additional ingredients (e.g., glycerol) may need to be considered to improve their viability during the freeze-drying process and extended storage.

Cold shock, metabolic injury, and the change of cell permeability during either the freezing process prior to the drying process or the vacuum drying process, can lead to damage of bacteria cells. Additionally, the ice crystal formation during freezing and the removal of water, which results in a change of hydrophilic macromolecules in cells, may also lead to the loss of viability. Nevertheless, our study showed that the viability of both bacteria was maintained at a level larger than 6 log CFU/g, which indicates that the integrated process shows promise for maintaining probiotic cells. Furthermore, probiotics in a freeze-dried form are more suitable for long-term preservation than in wet-form hydrogels.

Texture Profile Analysis

Texture profile analysis was conducted to understand the mechanical properties of the 3D printed G/A hydrogels before and after freeze-drying when subjected to mechanical force. The mechanical force in a sensory meaning can represent the mouthful feeling when a food product is compressed between human teeth. Hardness (g) is described as the maximum force needed to compress a food product. Significantly higher values were found among the 3D printed G/A hydrogels after freeze-drying (Table 7). Besides, the freeze-dried hydrogels of 3% G/A 2:1, 5% G/A 1:1, and 7% G/A 1:2 were significantly different from each other. The highest hardness was presented in 7% G/A 1:2 with a value of 21180.20 g for B. lactis and 25904.32 g for L. acidophilus. No significant difference was found between the gels with the two different bacteria.

Gumminess (g) (for hydrogels) and chewiness (g) (for freeze-dried capsules) encapsulated with B. lactis and L. acidophilus are displayed in Table 8. Gumminess is used to describe the energy required to disintegrate semi-solid foods, in our case, the 3D printed hydrogels, to a state ready for swallowing. Gumminess of the 3D printed G/A hydrogels were significantly different among 3% G/A 2:1, 5% G/A 1:1, and 7% G/A 1:2 for both B. lactis and L. acidophilus. Moreover, 3D printed hydrogels made with 7% G/A 1:2 had a significantly higher value of gumminess with 1404.51 g and 1323.08 g for B. lactis and L. acidophilus, respectively. The lowest gumminess values were found in 3% G/A 2:1 with 520.62 g and 423.35 g for B. lactis and L. acidophilus. Hydrogels with higher gumminess are likely to appeal to consumers who look for a gummy texture. However, hydrogels with lower gumminess may be more suitable for individuals with chewing difficulty. Similarly, chewiness is the energy required to masticate a solid food, in our case, the freeze-dried hydrogels, to a state ready for swallowing. The highest chewiness was found in 7% G/A 1:2 with a value of 3235.25 g and 3679.46 g for B. lactis and L. acidophilus. Freeze-dried hydrogels with higher chewiness mean more time is needed to masticate.

Overall, the hydrogels changed from a semi-solid state to a solid-like state after freeze-drying, which was also indicated by the increase of hardness from texture profile analysis and the significant reduction in water activity. It should be noted that texture profile analysis cannot thoroughly mimic the chewing behavior in realistic because it does not take the saliva and enzymes in the mouth into account. As long as the freeze-dried hydrogels interact with moisture, the rehydration will change the texture to some extent. Finally, no significant differences were found for either gumminess or chewiness based on the two bacteria.

Conclusions

In this Example, we were able to obtain convenient, hydrogel-based food carriers to deliver probiotics by using an integrated manufacturing processes of encapsulation, 3D printing, and freeze-drying. The formulations of 3% G/A 2:1, 5% G/A 1:1, and 7% G/A 1:2 was shown great potential for such purpose. Overall, the viable counts of bacteria were maintained at a level larger than 9 log CFU/g and 6 log CFU/g for $B.$ $lactis$ and $L.$ $acidophilus$, respectively, which aligns with the definition of probiotic food. The organism of $B.$ $lactis$ was able to maintain at a level of >6 log CFU/g upon 8 weeks of storage at room temperature. After encapsulating with bacteria, the rheological properties, flow behavior, and viscoelasticity of the G/A hydrogels did not significantly change. However, the yield stress of the G/A hydrogels was lower when the bacteria were encapsulated. Freeze-drying increased the hardness and reduced the water activity of the hydrogels. Therefore, this study shown that the integrated manufacturing consisting of encapsulation, 3D printing, and freeze-drying could be considered a feasible approach to protect probiotics within an edible hydrogel matrix. The outcome of this study shows its potential to develop a shelf-stable and convenient product or supplement to deliver customized strains and dosage to convey the health benefits of probiotics.

TABLE 5

Estimated yield stress of the gelatin-alginate (G/A) hydrogels without and with $B.$ $lactis$ and $L.$ $acidophilus$.

| | | With | |
|---|---|---|---|
| | Without | $B.$ $lactis$ | $L.$ $acidophilus$ |
| 3% G/A 2:1 | $65.09 \pm 1.42^{Ca}$ | $40.61 \pm 1.59^{Cc}$ | $57.78 \pm 1.46^{Cb}$ |
| 5% G/A 1:1 | $215.80 \pm 0.95^{Ba}$ | $202.99 \pm 5.66^{Bb}$ | $211.68 \pm 2.07^{Ba}$ |
| 7% G/A 1:2 | $521.35 \pm 3.44^{Aa}$ | $454.41 \pm 4.43^{Ac}$ | $493.75 \pm 3.58^{Ab}$ |

Values with different uppercase superscripts within the same column and lowercase superscripts within the same row are statistically different from another (p < 0.05). Mean ± Standard deviation values from triplicates.

TABLE 6

Water activity ($a_w$) of the 3D printed gelatin-alginate (G/A) hydrogels encapsulated with the two probiotics of $B.$ $lactis$ and $L.$ $acidophilus$ before and after freeze-drying.

| | $B.$ $lactis$ | | $L.$ $acidophilus$ | |
|---|---|---|---|---|
| | 3D printed | freeze-dried | 3D printed | freeze-dried |
| 3% G/A 2:1 | $0.997 \pm 0.001^{A}$ | $0.091 \pm 0.016^{B}$ | $0.998 \pm 0.002^{A}$ | $0.101 \pm 0.009^{B}$ |
| 5% G/A 1:1 | $0.996 \pm 0.001^{A}$ | $0.048 \pm 0.006^{D}$ | $0.995 \pm 0.002^{A}$ | $0.066 \pm 0.004^{C}$ |
| 7% G/A 1:2 | $0.996 \pm 0.002^{A}$ | $0.071 \pm 0.001^{C}$ | $0.994 \pm 0.003^{A}$ | $0.089 \pm 0.015^{B}$ |

Values with different superscripts within the same bacteria are statistically different from another (p < 0.05). Mean ± Standard deviation values from triplicates.

TABLE 7

Hardness (g) of the 3D printed gelatin-alginate (G/A) hydrogels encapsulated with $B.$ $lactis$ and $L.$ $acidophilus$ before and after freeze-drying.

| | $B.$ $lactis$ | | $L.$ $acidophilus$ | |
|---|---|---|---|---|
| | 3D printed | freeze-dried | 3D printed | freeze-dried |
| 3% G/A 2:1 | $794.35 \pm 106.77^{D}$ | $8917.62 \pm 1209.53^{C}$ | $641.15 \pm 46.15^{D}$ | $8517.70 \pm 267.85^{C}$ |
| 5% G/A 1:1 | $1350.70 \pm 185.68^{D}$ | $13625.53 \pm 826.85^{B}$ | $1126.26 \pm 104.22^{D}$ | $15757.82 \pm 1395.56^{B}$ |
| 7% G/A 1:2 | $2226.58 \pm 168.54^{D}$ | $21180.20 \pm 1492.91^{A}$ | $2208.24 \pm 41.20^{D}$ | $25904.32 \pm 645.067^{A}$ |

Values with different superscripts within the same bacteria are statistically different from another (p < 0.05). Mean ± Standard deviation values from triplicates.

TABLE 8

Gumminess (g) for 3D printed and chewiness (g) for freeze-dried of the gelatin-alginate (G/A) hydrogels encapsulated with $B.$ $lactis$ and $L.$ $acidophilus$.

| | $B.$ $lactis$ | | $L.$ $acidophilus$ | |
|---|---|---|---|---|
| | 3D printed Gumminess | freeze-dried Chewiness | 3D printed Gumminess | freeze-dried Chewiness |
| 3% G/A 2:1 | $520.62 \pm 135.21^{C}$ | $1931.16 \pm 410.27^{b}$ | $423.35 \pm 35.42^{C}$ | $1293.00 \pm 114.49^{c}$ |
| 5% G/A 1:1 | $831.72 \pm 98.66^{B}$ | $1901.51 \pm 287.74^{b}$ | $671.52 \pm 110.90^{B}$ | $2203.15 \pm 232.95^{b}$ |
| 7% G/A 1:2 | $1404.51 \pm 100.15^{A}$ | $3235.25 \pm 281.31a^{a}$ | $1323.08 \pm 28.60^{A}$ | $3679.46 \pm 414.07^{a}$ |

Values with different superscripts (uppercase for gumminess and lowercase for chewiness) within the same bacteria are statistically different from another (p < 0.05). Mean ± Standard deviation values from triplicates.

TABLE 9

Moisture content (%) for the 3D printed gelatin-alginate (G/A) hydrogels encapsulated with *B. lactis* and *L. acidophilus*.

|  | *B. lactis* | *L. acidophilus* |
|---|---|---|
| 3% G/A 2:1 | 96.89 ± 0.25[A] | 96.77 ± 0.03[A] |
| 5% G/A 1:1 | 94.89 ± 0.03[B] | 94.98 ± 0.04[B] |
| 7% G/A 1:2 | 92.81 ± 0.05[C] | 92.93 ± 0.07[C] |

Values with different superscripts in the same column are statistically different from another ($p < 0.05$). Mean ± Standard deviation values from triplicates.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A method of preparing a shelf-stable hydrogel, comprising:
   obtaining two or more hydrogel precursors comprising gelatin and alginate;
   mixing the hydrogel precursors with an active ingredient to form a mixture, wherein the active ingredient comprises a probiotic, wherein the probiotic is *Bifidobacterium lactis*;
   crosslinking the hydrogel precursors into a gelatin-alginate hydrogel comprising from 3% to 7% w/w gelatin and alginate in a ratio from 2:1 to 1:2;
   3D printing the hydrogel; and
   freeze-drying the hydrogel;
   wherein the hydrogel is food grade, and wherein the probiotic has a cell viability of at least $10^6$ CFU/g and at least 60% of a starting viable cell count after 8 weeks of storage at room temperature.

2. The method of claim 1, wherein the two or more hydrogel precursors have a storage modulus (G') higher than loss modulus (G"), with a loss factor (tan δ=G"/G') in the range of 0.48 to 0.61 at the frequency sweep of 15 to 40 rad/s.

3. The method of claim 1, further comprising centrifuging the mixture.

4. The method of claim 1, further comprising sterilizing the hydrogel precursor.

5. The method of claim 1, wherein the active ingredient further comprises an enzyme, a vitamin, a prebiotic, or a combination thereof.

6. The method of claim 1, wherein the further comprising mixing an additive, wherein the additive comprises a colorant, a scent, and/or a flavoring.

7. The method of claim 1, wherein the crosslinking of the hydrogel precursor occurs prior to 3D printing.

8. The method of claim 1, wherein the crosslinking of the hydrogel precursor occurs during 3D printing.

9. The method of claim 1, wherein the 3D printing is droplet-based, extrusion-based, stereolithography bioprinting, multi-printhead printing, or a combination thereof.

10. A shelf-stable hydrogel composition, comprising:
    a freeze-dried, 3D printed food grade gelatin-alginate hydrogel comprising an active ingredient, wherein the hydrogel comprises from 3% to 7% w/w gelatin and alginate in a ratio from 2:1 to 1:2; wherein the active ingredient comprises a probiotic, wherein the probiotic is *Bifidobacterium lactis*; and wherein the probiotic has a cell viability of at least $10^6$ CFU/g and at least 60% of a starting viable cell count after 8 weeks of storage at room temperature.

11. The shelf-stable hydrogel composition of claim 10, wherein the active ingredient further comprises an enzyme, a vitamin, a prebiotic, or a combination thereof.

12. The shelf-stable hydrogel composition of claim 11, further comprising an additive; wherein the additive comprises a colorant, a scent, and/or a flavoring.

\* \* \* \* \*